United States Patent
Cheon et al.

(10) Patent No.: US 11,033,250 B2
(45) Date of Patent: Jun. 15, 2021

(54) ULTRASOUND APPARATUS AND ULTRASOUND MEDICAL IMAGING METHOD FOR IDENTIFYING VIEW PLANE OF ULTRASOUND IMAGE BASED ON CLASSIFIERS

(71) Applicant: SAMSUNG ELECTRONICS CO., LTD., Suwon-si (KR)

(72) Inventors: Min-su Cheon, Yongin-si (KR); Ho-kyung Kang, Seoul (KR); Yu-mi Sohn, Seongnam-si (KR); Jong-geun Park, Seoul (KR); Young-yoon Lee, Yongin-si (KR); Jin-woo Yim, Seongnam-si (KR); Ki-won Sohn, Seoul (KR); Hojjat Alireza, Seoul (KR); Jae-young Choi, Uiwang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1112 days.

(21) Appl. No.: 14/669,621

(22) Filed: Mar. 26, 2015

(65) Prior Publication Data

US 2015/0272546 A1 Oct. 1, 2015

(30) Foreign Application Priority Data

Mar. 26, 2014 (KR) .................. 10-2014-0035379

(51) Int. Cl.
*A61B 8/00* (2006.01)
*A61B 8/08* (2006.01)
(Continued)

(52) U.S. Cl.
CPC .............. *A61B 8/469* (2013.01); *A61B 8/463* (2013.01); *A61B 8/465* (2013.01); *A61B 8/5207* (2013.01); *A61B 8/5223* (2013.01);
*A61B 8/54* (2013.01); *A61B 8/565* (2013.01); *G06K 9/3233* (2013.01); *G06K 9/6282* (2013.01); *G06T 7/0012* (2013.01); *G06T 7/246* (2017.01); *A61B 8/0883* (2013.01); *G01S 7/52073* (2013.01);
(Continued)

(58) Field of Classification Search
CPC .............................. A61B 5/469; A61B 8/0883
See application file for complete search history.

(56) References Cited

U.S. PATENT DOCUMENTS 8,073,215 B2   12/2011   Lu et al.
9,498,187 B2   11/2016   Smith et al.
(Continued)

FOREIGN PATENT DOCUMENTS

JP      2019-22824 A      2/2019
KR   10-2009-0029673 A    3/2009
(Continued)

OTHER PUBLICATIONS

Communication dated Feb. 22, 2021 issued by the Korean Intellectual Property Office in counterpart Korean Application No. 10-2014-0035379 English Translation.

*Primary Examiner* — James M Kish
(74) *Attorney, Agent, or Firm* — Sughrue Mion, PLLC

(57) ABSTRACT

An ultrasound medical imaging method includes: displaying an ultrasound image on a screen; determining a view plane, on which the displayed ultrasound image is captured, among view planes; and setting a region of interest corresponding to the determined view plane on the ultrasound image.

13 Claims, 27 Drawing Sheets

(51) Int. Cl.
*G06T 7/00* (2017.01)
*G06K 9/62* (2006.01)
*G06K 9/32* (2006.01)
*G06T 7/246* (2017.01)
*G01S 7/52* (2006.01)

(52) U.S. Cl.
CPC ............... *G06K 2209/051* (2013.01); *G06T 2207/10132* (2013.01); *G06T 2207/20081* (2013.01); *G06T 2207/20104* (2013.01); *G06T 2207/30048* (2013.01)

(56) References Cited

U.S. PATENT DOCUMENTS

| | | | |
|---|---|---|---|
| 10,799,218 B2 | 10/2020 | Schneider et al. | |
| 2006/0034513 A1* | 2/2006 | Cai | A61B 8/14 382/173 |
| 2006/0064017 A1 | 3/2006 | Krishnan et al. | |
| 2007/0127798 A1* | 6/2007 | Chakraborty | G06F 19/321 382/128 |
| 2009/0034808 A1 | 2/2009 | Zhou et al. | |
| 2009/0088640 A1 | 4/2009 | Park et al. | |
| 2009/0153548 A1* | 6/2009 | Rabben | A61B 8/14 345/419 |
| 2010/0125203 A1 | 5/2010 | Lee et al. | |
| 2010/0329521 A1 | 12/2010 | Beymer et al. | |
| 2011/0144498 A1* | 6/2011 | Ando | A61B 8/469 600/443 |
| 2013/0011033 A1 | 1/2013 | Beymer et al. | |
| 2013/0182935 A1* | 7/2013 | Wang | G06K 9/3233 382/133 |
| 2014/0122381 A1* | 5/2014 | Nowozin | G06N 20/00 706/12 |

FOREIGN PATENT DOCUMENTS

| | | | |
|---|---|---|---|
| KR | 10-2010-0056240 A | 5/2010 | |
| KR | 10-2013-0056676 A | 5/2013 | |

\* cited by examiner

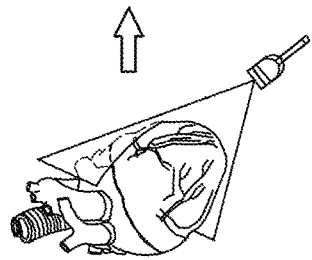
FIG. 1A
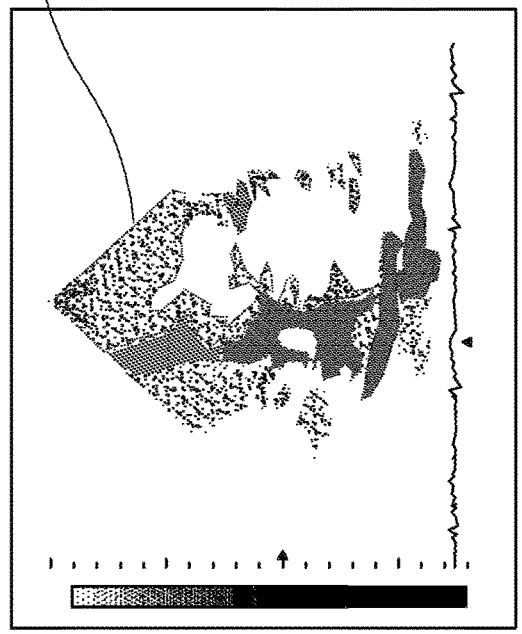
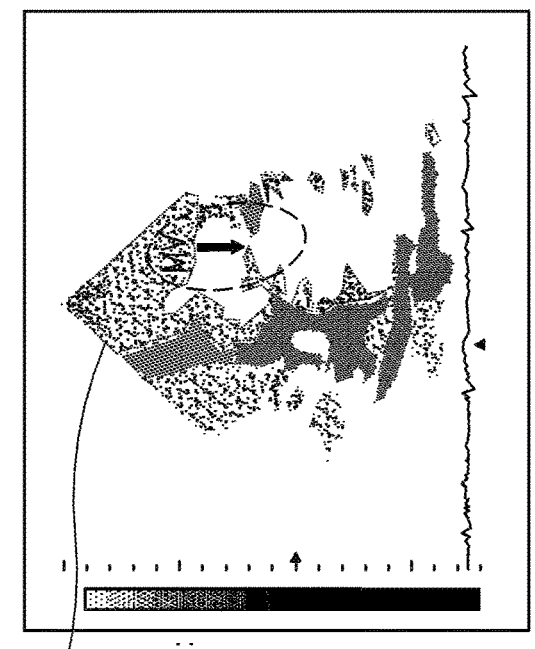
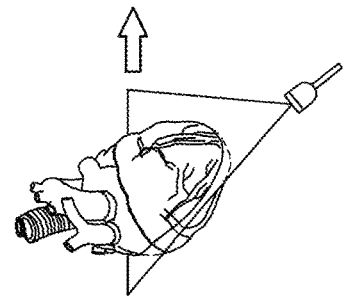
FIG. 1B
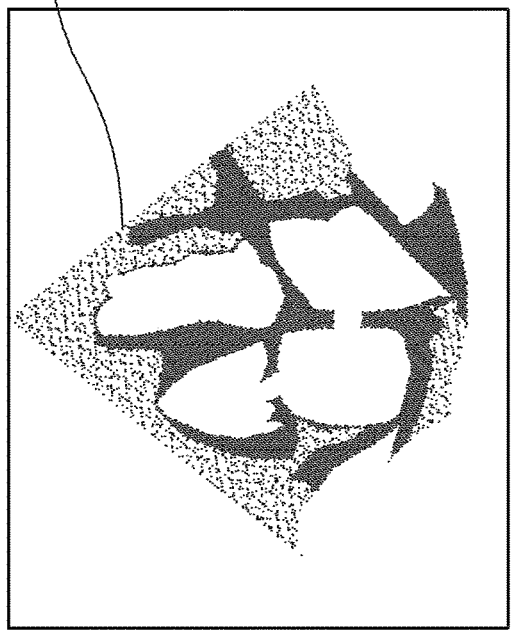
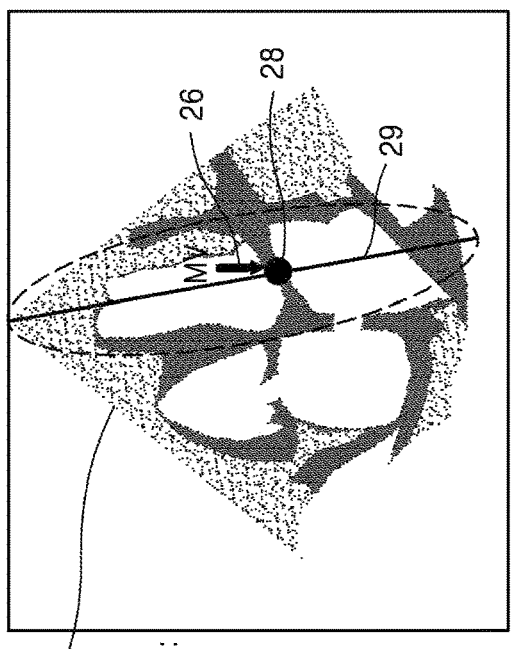

FIG. 4

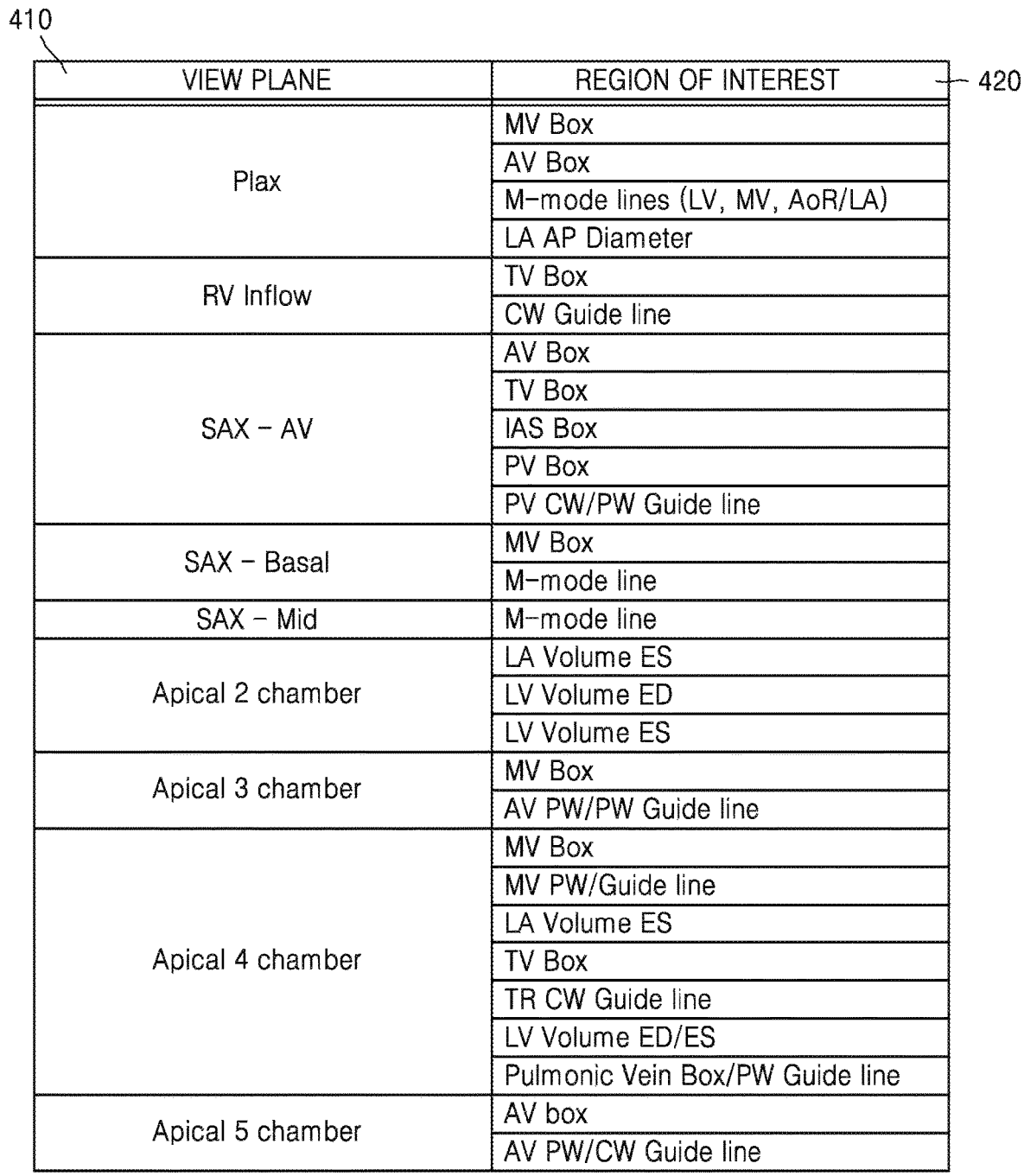

| VIEW PLANE | REGION OF INTEREST |
|---|---|
| Plax | MV Box |
|  | AV Box |
|  | M-mode lines (LV, MV, AoR/LA) |
|  | LA AP Diameter |
| RV Inflow | TV Box |
|  | CW Guide line |
| SAX – AV | AV Box |
|  | TV Box |
|  | IAS Box |
|  | PV Box |
|  | PV CW/PW Guide line |
| SAX – Basal | MV Box |
|  | M-mode line |
| SAX – Mid | M-mode line |
| Apical 2 chamber | LA Volume ES |
|  | LV Volume ED |
|  | LV Volume ES |
| Apical 3 chamber | MV Box |
|  | AV PW/PW Guide line |
| Apical 4 chamber | MV Box |
|  | MV PW/Guide line |
|  | LA Volume ES |
|  | TV Box |
|  | TR CW Guide line |
|  | LV Volume ED/ES |
|  | Pulmonic Vein Box/PW Guide line |
| Apical 5 chamber | AV box |
|  | AV PW/CW Guide line |

FIG. 6

| VIEW PLANE | ORDER OF SIMILAR VIEW PLANES |
|---|---|
| Apical 2 chamber (A2C) | A4C, A3C, MID, RVI, AOR, BAS, APE, SUP, LAX, IVC |
| Apical 3/5 chamber (A3C) | A2C, A4C, MID, SUP, BAS, RVI, APE, AOR, LAX, IVC |
| Apicla 4 chamber (A4C) | A3C, A2C, MID, SUP, BAS, RVI, APE, AOR, LAX, IVC |
| SAX-AV (AOR) | BAS, MID, APE, A2C, A3C, A4C, LAX, RVI, IVC, SUP |
| SAX-Basal (BAS) | MID, AOR, APE, A2C, A3C, A4C, LAX, RVI, IVC, SUP |
| SAX-Mid (MID) | BAS, APE, AOR, A2C, A3C, A4C, LAX, RVI, IVC, SUP |
| SAX-Apex (APE) | MID, BAS, AOR, RVI, SUP, A2C, A3C, A4C, LAX, IVC |
| PLAX (LAX) | SUP, IVC, A4C, A3C, A2C, MID, BAS, AOR, APE, RVI |
| IVC | MID, BAS, AOR, APE, RVI, SUP, A2C, A3C, A4C, LAX |
| RV Inflow (RVI) | MID, BAS, AOR, APE, IVC, SUP, A2C, A3C, A4C, LAX |
| Suprasternal view (SUP) | MID, BAS, AOR, APE, IVC, RVI, A2C, A3C, A4C, LAX |

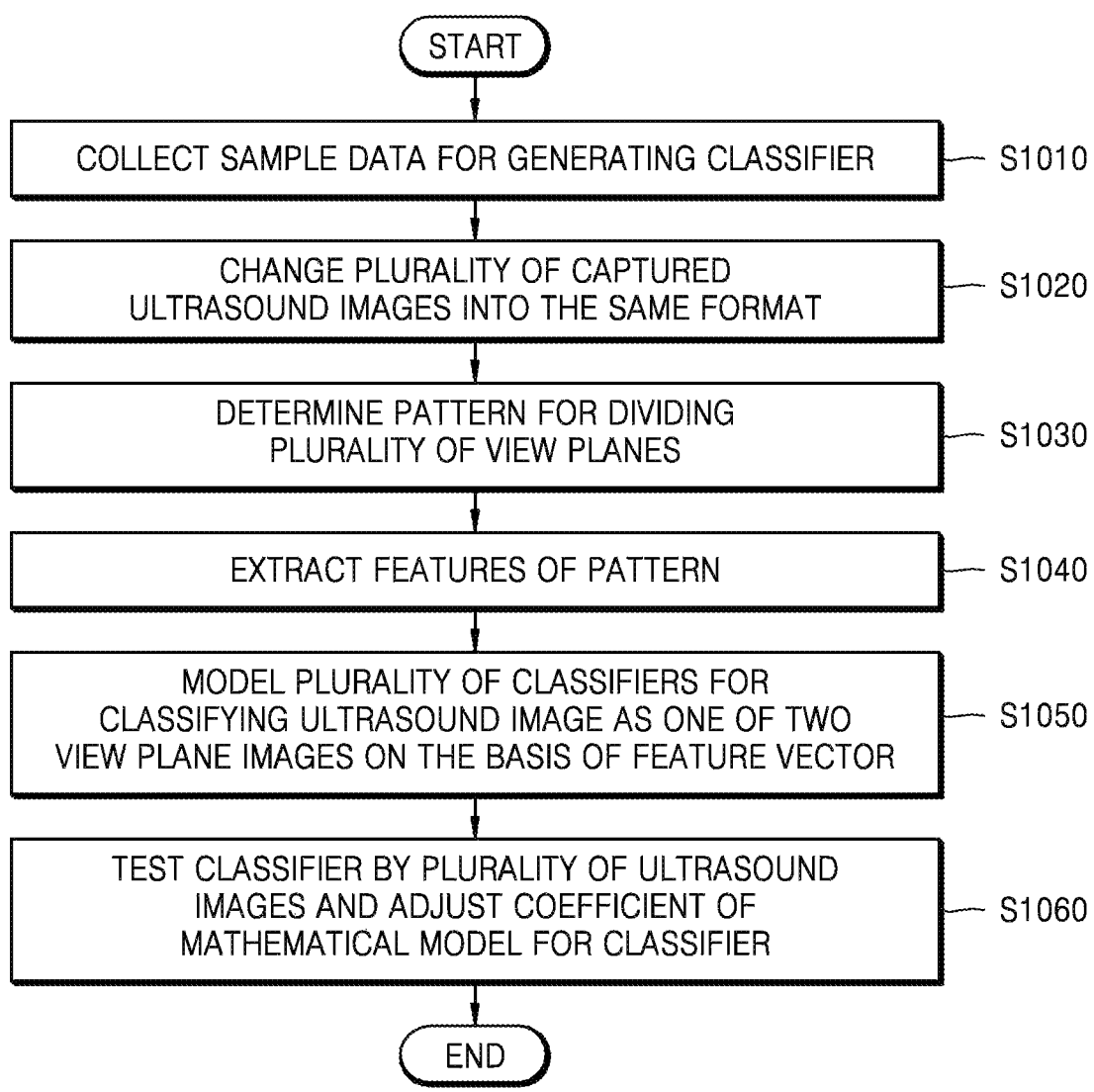

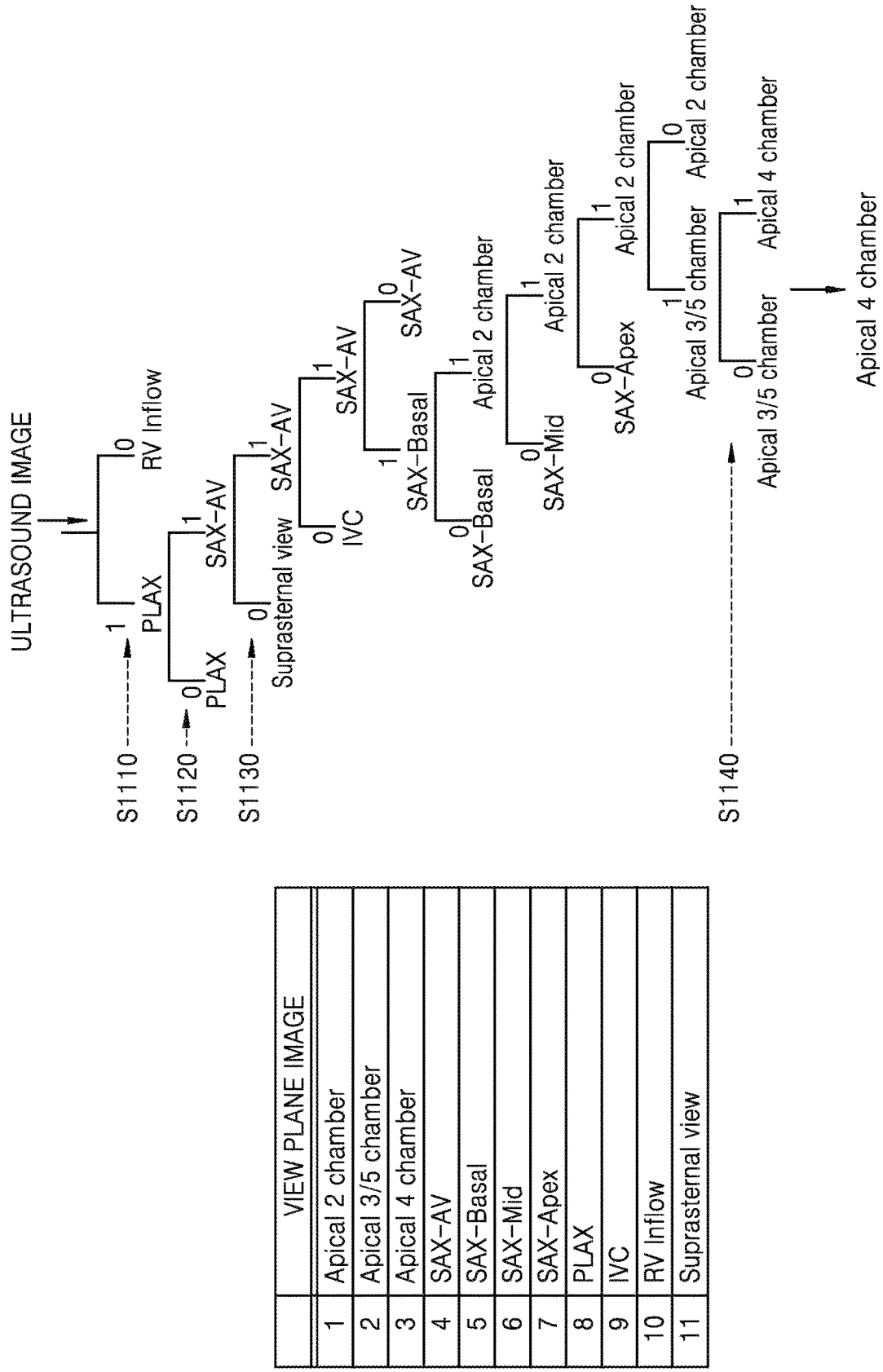

FIG. 12A

| | VIEW PLANE IMAGE | |
|---|---|---|
| 1 | Apical 2 chamber | (A2C) |
| 2 | Apical 3/5 chamber | (A3C) |
| 3 | Apical 4 chamber | (A4C) |
| 4 | SAX-AV | (AOR) |
| 5 | SAX-Basal | (BAS) |

FIG. 12B

| | CLASSIFIER | RESULTS |
|---|---|---|
| 1 | A2C vs A3C | A2C |
| 2 | A2C vs A4C | A2C |
| 3 | A2C vs AOR | A2C |
| 4 | A2C vs BAS | A2C |
| 5 | A4C vs AOR | A4C |
| 6 | AOR vs BAS | AOR |
| 7 | A4C vs BAS | A4C |
| 8 | A3C vs A4C | A4C |
| 9 | A3C vs AOR | A3C |
| 10 | A3C vs BAS | A3C |

FIG. 12C

| RANKING | VIEW CLASS | | SCORE |
|---|---|---|---|
| 1 | Apical 2 chamber | (A2C) | 4 |
| 2 | Apical 4 chamber | (A3C) | 3 |
| 3 | Apical 43/5 chamber | (A3C) | 2 |
| 4 | SAX-AV | (AOR) | 1 |
| 5 | SAX-Basal | (BAS) | 0 |

FIG. 13A

| | VIEW PLANE IMAGE | |
|---|---|---|
| 1 | Apical 2 chamber | (A2C) |
| 2 | Apical 3/5 chamber | (A3C) |
| 3 | Apical 4 chamber | (A4C) |
| 4 | SAX-AV | (AOR) |
| 5 | SAX-Basal | (BAS) |

FIG. 13B

| | CLASSIFIER | RESULTS |
|---|---|---|
| 1 | A2C vs A3C | A2C |
| 2 | A2C vs A4C | A4C |
| 3 | A2C vs AOR | AOR |
| 4 | A2C vs BAS | BAS |

FIG. 13C

| | CLASSIFIER | RESULTS |
|---|---|---|
| 1 | A3C vs A4C | A4C |
| 2 | A3C vs AOR | A3C |
| 3 | A3C vs BAS | BAS |

FIG. 13D

| | CLASSIFIER | RESULTS |
|---|---|---|
| 1 | A4C vs AOR | A4C |
| 2 | A4C vs BAS | A4C |

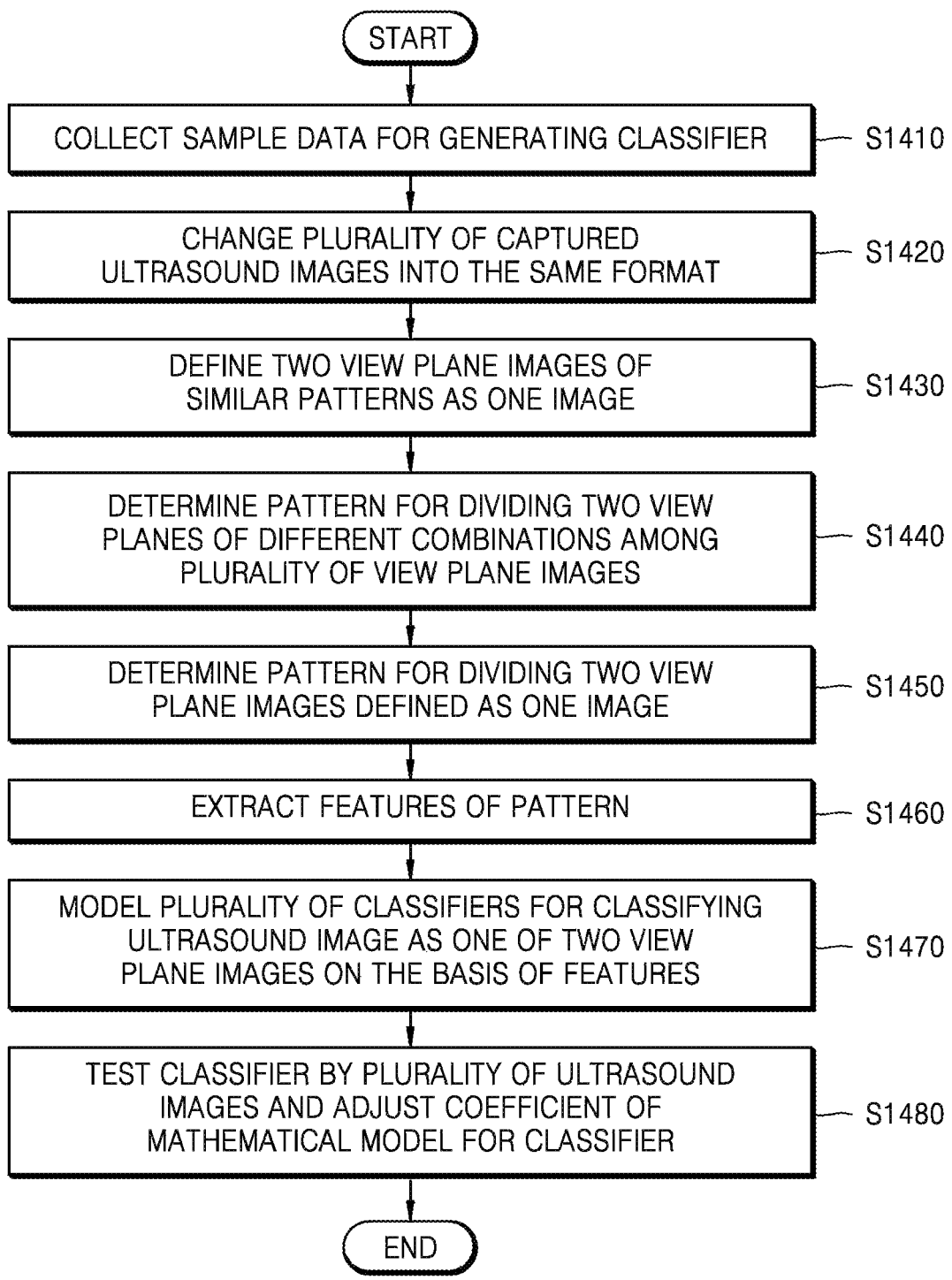

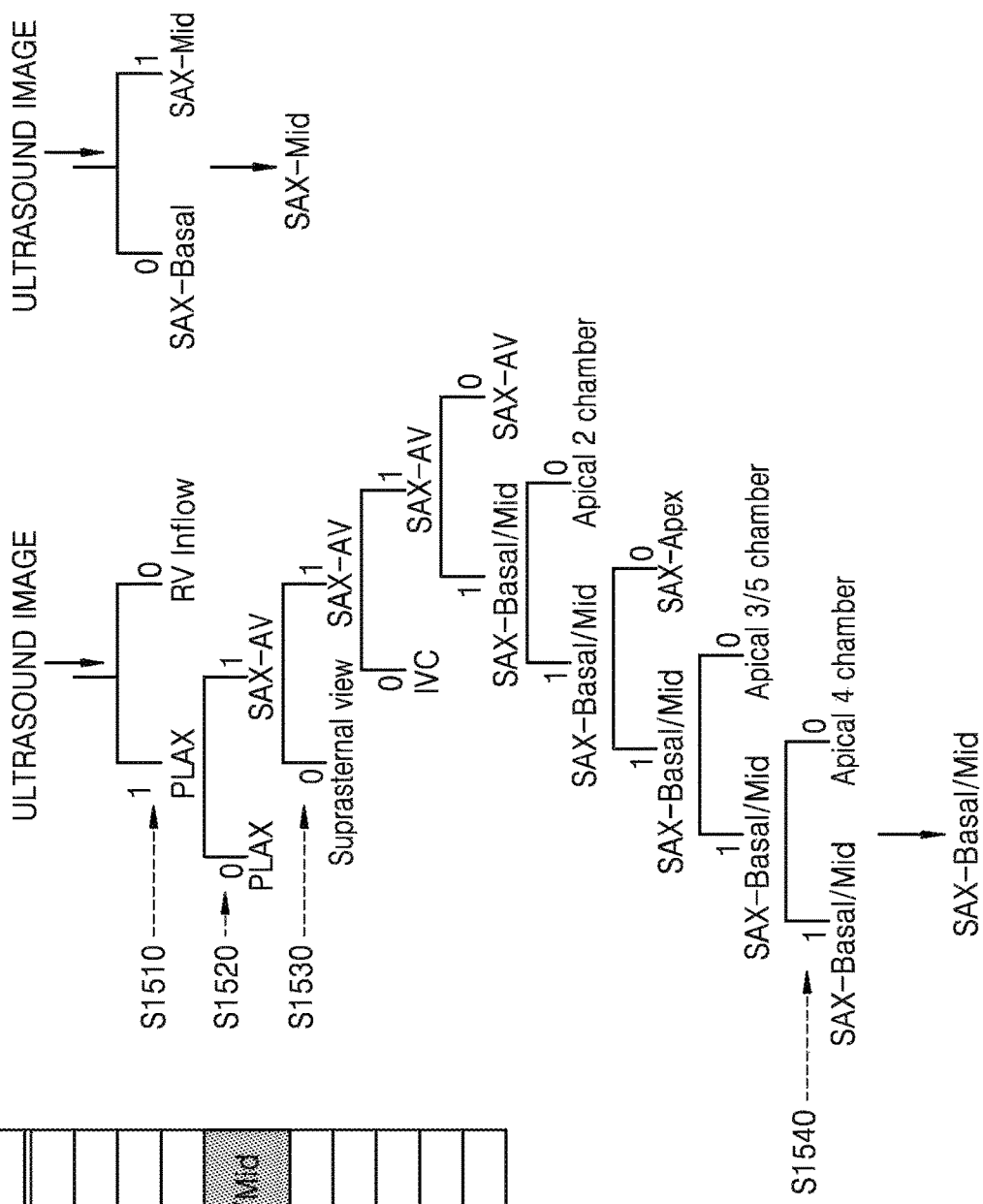

ULTRASOUND APPARATUS AND ULTRASOUND MEDICAL IMAGING METHOD FOR IDENTIFYING VIEW PLANE OF ULTRASOUND IMAGE BASED ON CLASSIFIERS

CROSS-REFERENCE TO RELATED APPLICATION

This application claims priority from Korean Patent Application No. 10-2014-0035379, filed on Mar. 26, 2014, in the Korean Intellectual Property Office, the disclosure of which is incorporated herein in its entirety by reference.

BACKGROUND

1. Field

One or more exemplary embodiments relate to ultrasound imaging, and, more particularly, to determining the type of the ultrasound image.

2. Description of the Related Art

An ultrasound diagnostic apparatus transmits an ultrasound signal from a surface of an object to a predetermined part in a body of the object and obtains a tomogram of a soft tissue or an image of a bloodstream by using information of an ultrasound signal reflected from a tissue in the body.

The ultrasound diagnostic apparatus is small and inexpensive and may display images in real time. Also, since the ultrasound diagnostic apparatus is very safe due to there being no exposure to X-rays or the like, the ultrasound diagnostic apparatus is widely used along with other image diagnostic apparatuses such as an X-ray diagnostic apparatus, a computed tomography (CT) scanner, a magnetic resonance imaging (MRI) apparatus, and a nuclear medicine diagnostic apparatus.

In ultrasound medical imaging, a user captures various cross-sectional images of a part or an organ of an object by varying the position, angle, or direction of an ultrasound probe. A user, for example, a doctor, diagnoses the condition of a patient based on the cross-sectional image of a part or an organ of the patient. Thus, the doctor needs to identify types of captured cross-sectional ultrasound images and to manually set a region of interest according to each cross-sectional image.

Further, the user may set a region of interest on an ultrasound image displayed on an ultrasound apparatus and measure an ultrasound image in the set region by using a user interface. In this case, whenever an ultrasound image is newly captured, the user has to manually set again a region of interest of interest to be measured on the newly-captured ultrasound image.

However, a plurality of such regions may need to be set on one ultrasound image, and a region of interest may have to be set in a different way for each part to be measured. Therefore, the user may need to frequently operate a control panel to set the regions of interest, which may be cumbersome and time consuming.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments include methods and ultrasound apparatuses for recognizing an ultrasound image, which may recognize the type of the ultrasound image based on the features of the ultrasound image.

According to one or more exemplary embodiments, a method for recognizing an ultrasound image includes: displaying an ultrasound image on a screen; determining a view plane, on which the displayed ultrasound image is captured, among a plurality of view planes; and setting at least one of a plurality of regions of interest corresponding to the determined view plane on the ultrasound image.

The determining of the view plane may include determining the view plane based on a result value of a series of classifiers that classify the ultrasound image as one of a predetermined number of view plane images, and the predetermined number of view plane images may be selected as different combinations among a plurality of view plane images corresponding to the plurality of view planes.

The predetermined number may be two.

The method may further include: displaying a user interface for changing the determined view plane into one of the plurality of view planes on the screen; and receiving a user input for selecting one of the plurality of view planes and setting at least one of a plurality of regions of interest corresponding to the selected view plane on the ultrasound image.

The user interface for changing the determined view plane into one of the plurality of view planes may include identification information of the plurality of view planes, and the identification information of the plurality of view planes may be arranged based on an order preset corresponding to the determined view plane.

The order of the plurality of view planes preset corresponding to the determined view plane may be determined based on a similarity to a view plane image corresponding to the determined view plane.

The setting of the at least one of the plurality of regions of interest corresponding to the determined view plane on the ultrasound image may include: acquiring information about a plurality of regions of interest corresponding to the view plane; determining a position of the plurality of regions of interest in the ultrasound image based on the information about the plurality of regions of interest; and displaying an indicator representing at least one of the plurality of regions of interest on the ultrasound image based on the position of the plurality of regions of interest.

The method may further include: displaying a user interface for changing the region of interest set on the ultrasound image into one of the plurality of regions of interest corresponding to the determined view plane; and receiving a user input for selecting one of the plurality of regions of interest corresponding to the determined view plane and setting the selected region of interest on the ultrasound image based on the position of the plurality of regions of interest.

The setting of the at least one of the plurality of regions of interest corresponding to the determined view plane on the ultrasound image may include: calculating a sum of pixel values in a row or a column of the ultrasound image; determining a position of the plurality of regions of interest in the ultrasound image based on the sum of the pixel values in the row or the column; and displaying an indicator representing at least one of the plurality of regions of interest at the determined position.

The method may further include: displaying an indicator representing the at least region of interest set on the ultrasound image, on the ultrasound image; receiving a user input for adjusting a position of the displayed indicator; and adjusting a position of the plurality of regions of interest based on the received user input.

According to one or more exemplary embodiments, an ultrasound apparatus includes: a display configured to display an ultrasound image on a screen; an image determiner configured to determine a view plane, on which the displayed ultrasound image is captured, among a plurality of view planes; and a controller configured to set at least one of a plurality of regions of interest corresponding to the determined view plane on the ultrasound image.

The image determiner may include a series of classifiers configured to classify the ultrasound image as one of a predetermined number of view plane images, the controller may determine the view plane, on which the ultrasound image is captured, based on a result value of the series of classifiers, and the predetermined number of view plane images may be selected as different combinations among a plurality of view plane images corresponding to the plurality of view planes.

The display may display a user interface for changing the determined view plane into one of the plurality of view planes on the screen, and the controller may receive a user input for selecting one of the plurality of view planes and set at least one of a plurality of regions of interest corresponding to the selected view plane on the ultrasound image.

The controller may acquire information about a plurality of regions of interest corresponding to the view plane and determine a position of the plurality of regions of interest in the ultrasound image based on the information about the plurality of regions of interest, and the display may display an indicator representing at least one of the plurality of regions of interest on the ultrasound image based on the position of the plurality of regions of interest.

The display may display a user interface for changing the region of interest set on the ultrasound image into one of the plurality of regions of interest corresponding to the determined view plane, and the controller may receive a user input for selecting one of the plurality of regions of interest corresponding to the determined view plane and set the selected region of interest on the ultrasound image based on the position of the plurality of regions of interest.

The controller may calculate a sum of pixel values in a row or a column of the ultrasound image, determine a position of the plurality of regions of interest in the ultrasound image based on the sum of the pixel values in the row or the column, and display an indicator representing at least one of the plurality of regions of interest at the determined position.

The display may display an indicator representing the at least one region of interest set on the ultrasound image, on the ultrasound image, the ultrasound apparatus may further include a user input unit configured to receive a user input for adjusting a position of the displayed indicator, and the controller may adjust a position of the plurality of regions of interest based on the received user input.

BRIEF DESCRIPTION OF THE DRAWINGS

The discussed above aspects and/or other aspects will become more apparent by describing certain exemplary embodiments with reference to the accompanying drawings, in which:

FIGS. 1A and 1B illustrate an example of automatically recognizing a view plane of an ultrasound image by an ultrasound apparatus according to an exemplary embodiment;

FIG. 4 is a diagram illustrating an example of a region of interest that may be extracted corresponding to a view plane and a type of a view plane according to an exemplary embodiment;

FIG. 6 is a diagram illustrating the order of view plane images having similar features with respect to one view plane image according to an exemplary embodiment;

FIG. 10 is a flowchart of a method for determining a classifier according to an exemplary embodiment;

FIGS. 11A and 11B illustrate a method for determining a view plane of an ultrasound image by using a classifier according to an exemplary embodiment;

FIGS. 12A, 12B, and 12C illustrate a method for determining a view plane of an ultrasound image by using a classifier according to another exemplary embodiment;

FIGS. 13A, 13B, 13C, and 13D illustrate a method for determining a view plane of an ultrasound image by using a classifier according to another exemplary embodiment;

FIG. 14 is a flowchart of a method for determining a classifier according to an exemplary embodiment;

FIGS. 15A, 15B, and 15C illustrate an example of a method for determining a view plane of an ultrasound image by using a classifier according to another exemplary embodiment;

DETAILED DESCRIPTION

Figure 2:
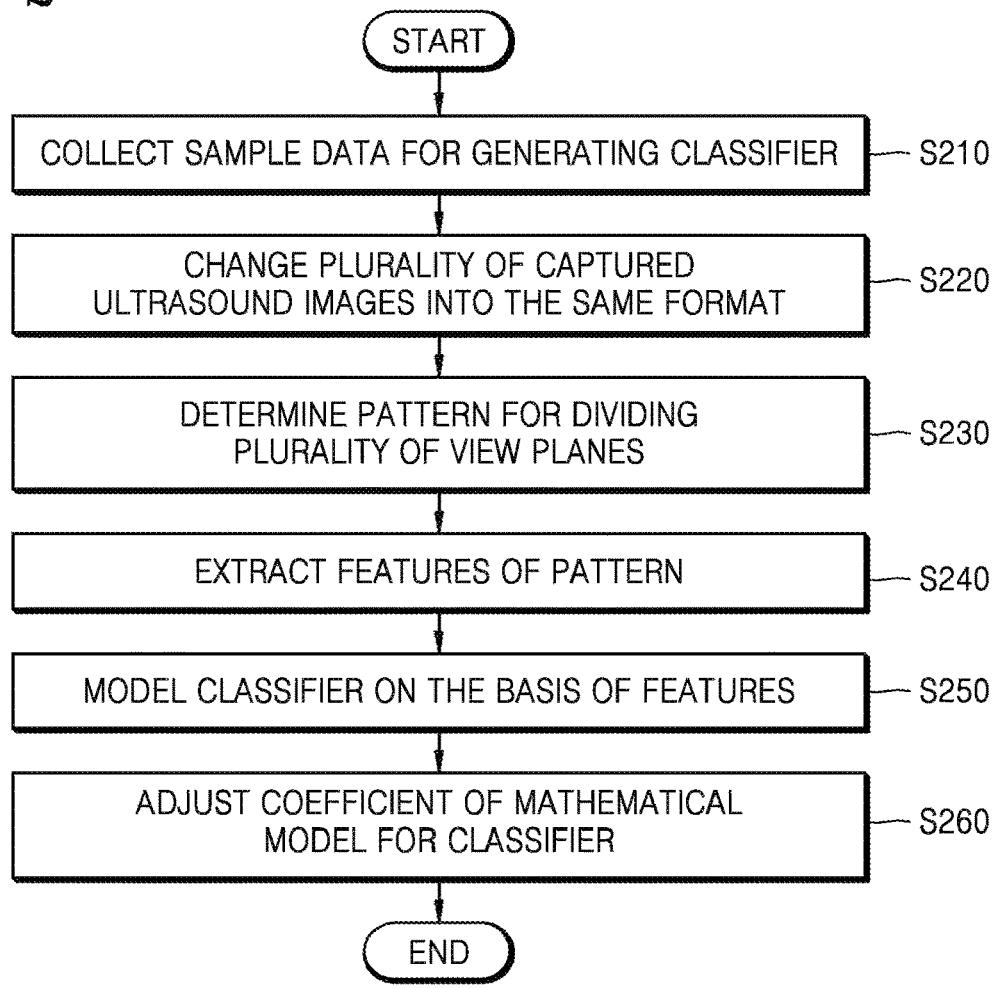
FIG. 2 is a flowchart of a method for determining a classifier by an ultrasound apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions are not described in detail since they would obscure the description with unnecessary detail.

As used herein, expressions such as "at least one of," when preceding a list of elements, modify the entire list of elements and do not modify the individual elements of the list.

When something "comprises" or "includes" a component, another component may be further included unless specified otherwise. Also, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is captured by using ultrasonic waves. Also, an "object" may include a person or an animal, or a part of a person or an animal. For example, the object may include an organ, such as a liver, a heart, a womb, a brain, a breast, or an abdomen, or a blood vessel. Also, the object may include a phantom. The phantom may refer to a material having a volume that is approximately the density and effective atomic number of a living thing, and may include a spherical phantom having a property similar to a human body.

Also, a "user" may be, but is not limited to, a medical expert, such as a doctor, a nurse, a medical laboratory technologist, or a medical imaging expert, or a technician who repairs a medical apparatus.

FIGS. 1A and 1B illustrate an example of automatically recognizing a view plane of an ultrasound image by an ultrasound apparatus 1000 according to an exemplary embodiment.

FIG. 1A illustrates an Apical 2 Chamber image of a heart that is captured through an ultrasound probe when the ultrasound probe is disposed in a vertical direction at a heart of an object.

FIG. 1B illustrates an Apical 4 Chamber image of the heart that is captured through the ultrasound probe when the ultrasound probe is disposed obliquely in a horizontal direction at the heart of the object.

As illustrated in FIGS. 1A and 1B, even when an ultrasound image of the same organ is captured, the acquired ultrasound image may have different patterns according to the positions, directions, or angles of the ultrasound probe.

For example, an ultrasound image 12 illustrated in FIG. 1A has a pattern in which a left ventricle and a left atrium appear vertically with the center of a mitral valve, while an ultrasound image 22 illustrated in FIG. 1B has a pattern in which all of left and right atriums and left and right ventricles appear.

Figure 29:
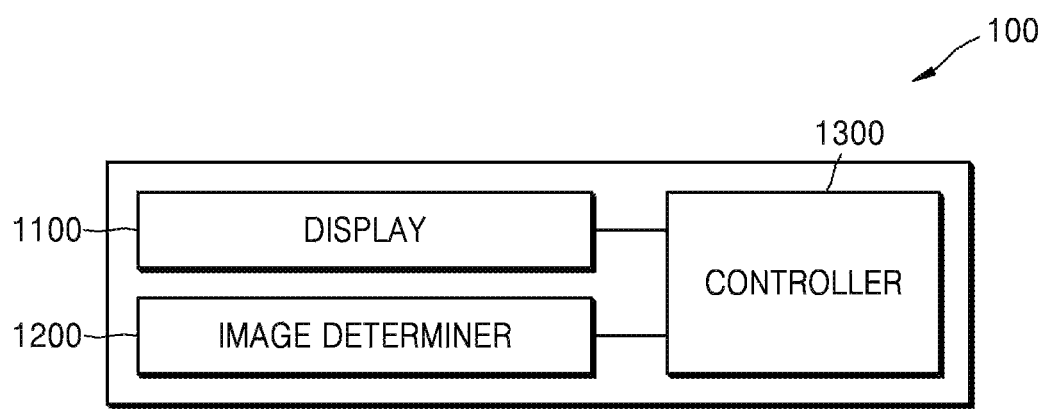
FIG. 29 is a block diagram of an ultrasound apparatus according to an exemplary embodiment.
Figure 30:
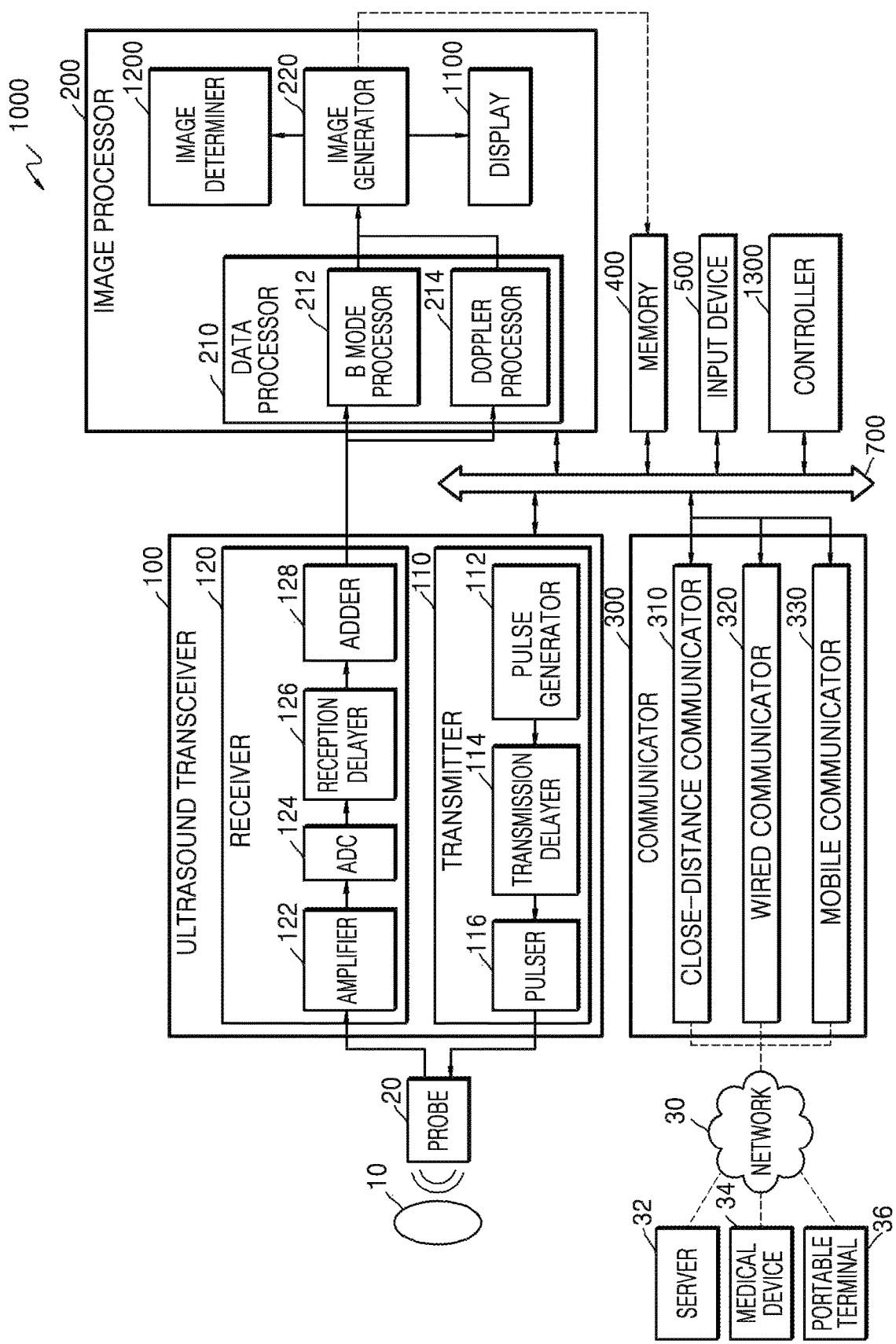
FIG. 30 is a block diagram of an ultrasound apparatus according to another exemplary embodiment.

With further reference to FIGS. 29 and 30, according to an exemplary embodiment, the ultrasound apparatus 1000 may determine a view plane on which the ultrasound image is captured. The view plane may refer to a plane that is generated according to the intersection between an ultrasound scan plane and the object. Also, the view plane may be specified by at least one of a part of the object and the position, direction, and angle of the ultrasound probe. Also, a view plane image may refer to an ultrasound image that is captured on the view plane.

According to an exemplary embodiment, the ultrasound apparatus 1000 may determine the view plane, on which the ultrasound image is captured, based on a unique pattern of the ultrasound image captured on each view plane.

For example, since the Apical 2 Chamber image illustrated in FIG. 1A has a pattern in which the left ventricle and the left atrium appear vertically, the ultrasound image 12 includes two dark regions in the vertical direction and a left heart wall is the brightest among the entire ultrasound image 12. On the other hand, since the Apical 4 Chamber image illustrated in FIG. 1B has a pattern in which all of the left and right atriums and the left and right ventricles appear, the ultrasound image 22 includes a bright cross pattern at a center thereof and a lower left region is the brightest among the entire ultrasound image 22. Accordingly, the ultrasound apparatus 1000 may determine the view plane, on which the ultrasound image is captured, based on the features of the captured ultrasound image.

According to an exemplary embodiment, the ultrasound apparatus 1000 may determine the view plane, on which the ultrasound image is captured, by using a plurality of classifiers having two view plane images of different combinations as class.

According to an exemplary embodiment, the ultrasound apparatus 1000 may display a user interface for selecting the view plane of the ultrasound image. Also, the ultrasound apparatus 1000 may change the view plane based on a user input.

According to an exemplary embodiment, the ultrasound apparatus 1000 may set a region of interest predetermined corresponding to the view plane on the ultrasound image.

For example, corresponding to the Apical 4 Chamber, a mitral valve, a tricuspid valve, or a left atrium volume may be set as the region of interest. Accordingly, when the view plane of the ultrasound image is determined as the Apical 4

Chamber, the ultrasound apparatus 1000 may extract the positions of the mitral valve, the tricuspid valve, and the left atrium volume on the ultrasound image. Then, the ultrasound apparatus 1000 may display an indicator predetermined corresponding to the region of interest and the view plane at the position of the region of interest. The indicator may have various shapes such as a point, a line, and a box.

For example, as illustrated in FIG. 1B, when the captured ultrasound image is determined as an Apical 4 Chamber image, the ultrasound apparatus 1000 may display an arrow 26 indicating the position 28 of the mitral valve and an abbreviation of the mitral valve at the position of the mitral valve in the ultrasound image, corresponding to the Apical 4 Chamber image, and display a line segment 29 connecting an apex of the ultrasound image and a bottom wall of the left atrium at the position of the mitral valve in the ultrasound image.

According to an exemplary embodiment, the ultrasound apparatus 1000 may display a user interface for selecting the region of interest. Also, the ultrasound apparatus 1000 may change the region of interest based on a user input.

Also, according to an exemplary embodiment, the ultrasound apparatus 1000 may detect the position of the region of interest corresponding to the view plane.

Also, according to an exemplary embodiment, the ultrasound apparatus 1000 may receive a user input for changing the region of interest and adjust the position of the region of interest according to the received user input.

FIG. 2 is a flowchart of a method for determining a classifier by the ultrasound apparatus 1000 according to an exemplary embodiment.

Referring to FIG. 2, in operation S210, the ultrasound apparatus 1000 may collect sample data for generating a classifier.

The sample data may include a plurality of ultrasound images captured on respective view planes. Also, the sample data may include an ultrasound image whose view plane is identified by the user.

The sample data may include an ultrasound image displayed on a screen. Also, the sample data may include an ultrasound image prior to scan conversion. Also, the sample data may include an average value of a plurality of frames constituting an ultrasound video image. Also, the sample data may include a plurality of frames of an ultrasound video image, which constitute a time period having the smallest pixel value change per hour. Also, the sample data may include an average value of a plurality of frames of an ultrasound video image, which constitute a time period having the smallest pixel value change per hour.

The sample data may be divided into a training set and a test set. The training set may be the sample data for extracting the features of the ultrasound image captured on the view plane and training the classifier. The test set may be the sample data for testing the performance of the generated classifier.

The ultrasound apparatus 1000 may acquire the sample data from an external server or a storage unit of the ultrasound apparatus 1000, and may acquire the sample data based on a user input.

In operation S220, the ultrasound apparatus 1000 may change the plurality of ultrasound images captured in operation S210 into the same format.

For example, the ultrasound apparatus 1000 may adjust the size of the plurality of ultrasound images to a predetermined size. Also, the ultrasound apparatus 1000 may adjust the contrast of the plurality of ultrasound images to a predetermined value. In this case, the ultrasound apparatus 1000 may use a histogram equalization method. Also, the ultrasound apparatus 1000 may remove a noise of the plurality of ultrasound images. In this case, the ultrasound apparatus 1000 may use a Gaussian smoothing method.

An operation of adjusting the format of the sample data to the same format may be referred to as a preprocessing operation.

In operation S230, the ultrasound apparatus 1000 may determine a pattern represented by a view plane image.

The pattern may refer to a unique pattern of the view plane by which the ultrasound image captured on the view plane may be discriminated from ultrasound images captured on other view planes. For example, since a left ventricle and a left atrium appear vertically in an Apical 2 Chamber image, the ultrasound image includes two dark regions in the vertical direction and has a pattern in which a left heart wall is the brightest among the entire ultrasound image. On the other hand, since all of left and right atriums and left and right ventricles appear in an Apical 4 Chamber image, the ultrasound image has a bright cross pattern at a center thereof and has a pattern in which a lower left region is the brightest among the entire ultrasound image. The ultrasound apparatus 1000 may determine a unique form of the view plane images as a pattern and determine a view plane, on which the ultrasound image is captured, based on the features of the pattern.

The unique form discriminated from other view plane images may be located in a partial region of the view plane image. For example, in an Apical 2 Chamber image, a left heart wall at a center position thereof is the brightest among the entire image.

Accordingly, the ultrasound apparatus 1000 may determine an unique form in a partial region of each view plane image as a pattern. Also, a plurality of patterns may be determined for one view plane.

In operation S240, the ultrasound apparatus 1000 may extract the features of the pattern determined in operation S230.

For example, the features may include a ranklet represented by the pattern, an average value, an edge histogram, an 8×8 resize image, and an homogeneity calculation value. Since the meanings of these terms may be easily understood by those of ordinary skill in the art, detailed descriptions thereof will be omitted herein.

The ultrasound apparatus 1000 may extract the features of the pattern of a view plane image from a plurality of ultrasound images captured on the same view plane.

For example, when the pattern appears in the entire region of the view plane image, the ultrasound apparatus 1000 may consecutively add the pixel values of the ultrasound image in the horizontal or vertical direction in the entire region of the ultrasound image. Also, the ultrasound apparatus 1000 may perform the same calculation on the plurality of ultrasound images captured on the same view plane. Then, the ultrasound apparatus 1000 may average the result values of the plurality of ultrasound images or determine the range of the result values to determine the features of the pattern of a view plane image.

Also, when the pattern appears in a partial region of the view plane image, the ultrasound apparatus 1000 may calculate the ranklet or the average value of pixels in the partial region. Also, the ultrasound apparatus 1000 may perform the same calculation on the plurality of ultrasound images captured on the same view plane. Then, the ultrasound apparatus 1000 may average the result values of the plurality of ultrasound images or determine the range of the result values to determine the features of the pattern of a view plane image.

In this case, a region in which the pattern is located may be set as a patch block region. The patch block region may refer to a region from which features will be extracted in the ultrasound image when the ultrasound apparatus 1000 determines the view plane of the ultrasound image.

Since the position of a pattern having a unique feature is different in each view plane image, a plurality of patch block regions may be provided. For example, about 10 to about 15 patch block regions may be provided.

Also, each pattern may have a plurality of features, and in this case, the plurality of features may be represented as a feature vector for each pattern.

In operation S250, the ultrasound apparatus 1000 may model a classifier for classifying an ultrasound image as one view plane image, based on the features of the pattern determined in operation S240.

For example, a mathematical model of the classifier may be generated so that the ultrasound image may be classified as the view plane image having more similar features than the extracted features when the features are extracted from the patch block region of the ultrasound image. The mathematical model of the classifier may be generated by various methods that are available in the technical field of the inventive concept.

Also, the ultrasound apparatus 1000 may model a classifier for classifying an ultrasound image as one view plane image, by using pattern recognition technology such as Neural Network or Decision Tree.

The ultrasound apparatus 1000 may model a classifier for selecting one of all view plane images that may be selected.

In operation S260, the ultrasound apparatus 1000 may test the classifier modeled in operation S250 by a plurality of ultrasound images and adjust a coefficient of the mathematical model of the classifier.

The ultrasound apparatus 1000 may set an ultrasound image, of which the view plane is identified, as an input value of the classifier and determine whether an output value of the classifier represents the identified view plane. The ultrasound apparatus 1000 may adjust the coefficient of the mathematical model of the classifier based on whether the output value of the classifier represents the identified view plane.

The ultrasound apparatus 1000 may determine the mathematical model so that the classifier may represent a minimum error, by performing a test on the classifier with respect to a plurality of ultrasound images whose view plane is identified.

The ultrasound apparatus 1000 may include integrated circuit (IC) logic or software logic for implementing the classifier.

Figure 3:
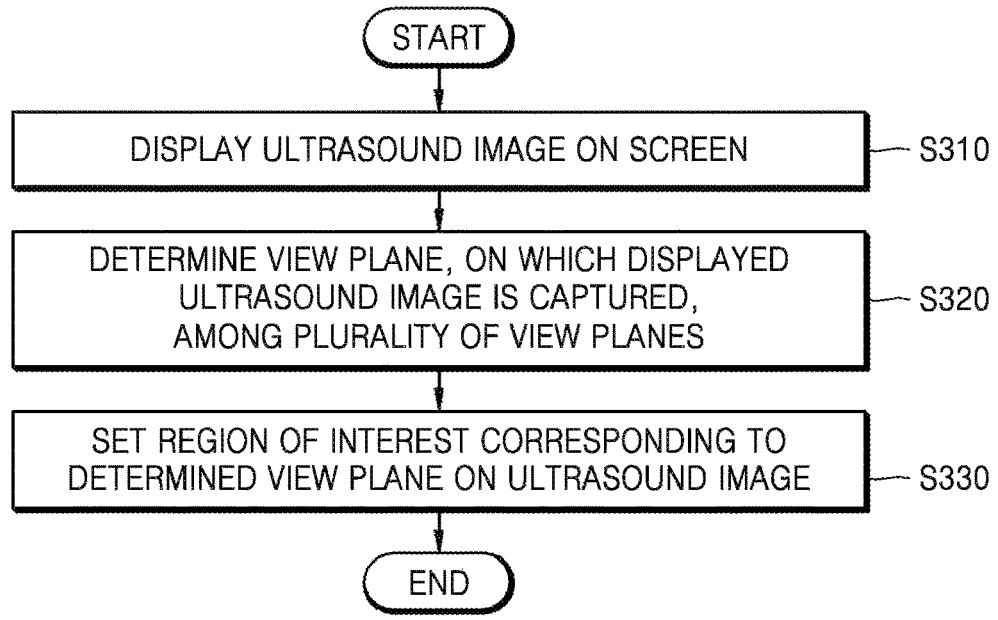
FIG. 3 is a flowchart of a method for recognizing an ultrasound image by an ultrasound apparatus according to an exemplary embodiment.

FIG. 3 is a flowchart of a method for recognizing an ultrasound image by the ultrasound apparatus 1000 according to an exemplary embodiment.

Referring to FIG. 3, in operation S310, the ultrasound apparatus 1000 may display an ultrasound image on the screen. The ultrasound image may be captured by the ultrasound apparatus 1000. Also, the ultrasound image may be received from an external device.

In operation S320, the ultrasound apparatus 1000 may determine a view plane, on which the displayed ultrasound image is captured, among a plurality of view planes.

The ultrasound apparatus 1000 may determine the view plane, on which the displayed ultrasound image is captured, by using a classifier that may classify an ultrasound image as a view plane image.

For example, the ultrasound apparatus 1000 may set a predetermined patch block in the displayed ultrasound image and extract ultrasound image data in the set patch block region. Then, the ultrasound apparatus 1000 may extract the features of the ultrasound image data in the patch block region. The ultrasound apparatus 1000 may calculate the edge histogram, the average value, and the ranklet of the ultrasound image data in the patch block region.

Then, the ultrasound apparatus 1000 may input the extracted features as an input value of the classifier. The classifier may classify an ultrasound image as one view plane image according to a preset mathematical model. The ultrasound apparatus 1000 may determine a view plane corresponding to the view plane image as the view plane on which the ultrasound image is captured.

In operation S330, the ultrasound apparatus 1000 may set at least one of a plurality of regions of interest corresponding to the determined view plane on the ultrasound image.

A plurality of regions of interest to be extracted corresponding to the view plane may be preset in the ultrasound apparatus 1000. Accordingly, the ultrasound apparatus 1000 may acquire information about the plurality of regions of interest to be extracted, based on the determined view plane. The information about the region of interest may include pattern information of the region of interest, display mode information of the region of interest, and position information of the region of interest.

The pattern information of the region of interest may include image information of the region of interest in the view plane image corresponding to the determined view plane. Also, the display mode information of the region of interest may include pattern information of an indicator to be displayed on the ultrasound image in order to represent the region of interest. Also, the position information of the region of interest may include size information of the region of interest and coordinate information of the position of the region of interest in the view plane image corresponding to the determined view plane.

The pattern information of the region of interest, the display mode information of the region of interest, and the position information of the region of interest may be stored corresponding to the view plane. For example, a mitral valve may be set as the region of interest, corresponding to a PLAX plane. Also, pattern information of the mitral valve, pattern information of an indicator for representing the mitral valve, and position information of the mitral valve may be prestored corresponding to the PLAX plane. Since the same part may have different patterns according to view plane images, the pattern information of the region of interest and the position information of the region of interest stored corresponding to the view plane may be different in the same region of interest.

Accordingly, the ultrasound apparatus 1000 may calculate the coordinates of the position of a plurality of regions of interest in the ultrasound image.

For example, the ultrasound apparatus 1000 may extract the coordinates of a region having a pattern similar to the pattern of the region of interest in the ultrasound image, based on the pattern information of the region of interest. Also, the ultrasound apparatus 1000 may extract the coordinate information of the position of the region of interest by using various image recognition methods for automatically detecting a region of interest in a medical image.

Also, the ultrasound apparatus 1000 may acquire the coordinates of the region of interest in the ultrasound image based on the position information of the region of interest.

The ultrasound apparatus 1000 may set at least one of the plurality of regions of interest extracted corresponding to the view plane on the ultrasound image. The region of interest among the plurality of regions of interest extracted corresponding to the view plane, which will be automatically set on the ultrasound image, may be preset in the ultrasound apparatus 1000. The region of interest to be automatically set on the ultrasound image corresponding to the view plane may be preset by the user or may be determined based on a usage pattern of the user.

The ultrasound apparatus 1000 may display the region of interest set on the ultrasound image, in the form of a point, a line, a box, or the like, based on the coordinate information of the region of interest on the ultrasound image.

FIG. 4 is a diagram illustrating an example of a region of interest 420 that may be extracted corresponding to a view plane and a type of a view plane 410 according to an exemplary embodiment.

Since the meanings of terms in FIG. 4 may be easily understood by those of ordinary skill in the art, detailed descriptions thereof will be omitted herein.

The ultrasound apparatus 1000 may determine a view plane 410 for an ultrasound image, and the view plane 410 may include, but is not limited to, Parasternal Long Axis View (PLAX), RV Inflow, Short Axis View (SAX)-AV, SAX-Basal, SAX-Mid, Apical 2 Chamber, Apical 3 chamber, Apical 4 Chamber, and Apical 5 chamber.

Also, a region of interest 420 to be extracted from the ultrasound image corresponding to the view plane may be preset in the ultrasound apparatus 1000.

Accordingly, when the view plane of the ultrasound image is determined, the ultrasound apparatus 1000 may acquire information about the region of interest corresponding to the view plane. Also, the ultrasound apparatus 1000 may calculate the coordinates of the position of the acquired region of interest in the ultrasound image.

For example, when the view plane of an input ultrasound image is determined as PLAX, the ultrasound apparatus 1000 may acquire information about a mitral valve, an atrio-ventricular node (AV), a left ventricle (LV), or a left atrium (LA), which is a region of interest preset corresponding to PLAX. Also, the ultrasound apparatus 1000 may calculate the coordinates of the position of a mitral valve, an atrio-ventricular node, a left ventricle, or a left atrium in the ultrasound image based on information about the region of interest. The information about the region of interest may include pattern information of the region of interest, display mode information of the region of interest, and position information of the region of interest.

Also, the ultrasound apparatus 1000 may set only a region of interest (which is predetermined corresponding to the view plane) among the plurality of regions of interest on the ultrasound image. For example, even when all of the regions of interest preset corresponding to the view plane are extracted from the ultrasound image, the ultrasound apparatus 1000 may set only one region of interest which is predetermined corresponding to the view plane among the extracted regions of interest on the ultrasound image. Since the region of interest is set on the ultrasound image, the ultrasound apparatus 1000 may display an indicator representing the set region of interest at the coordinates of the region of interest. Also, the ultrasound apparatus 1000 may display a user interface for the set region of interest.

Also, when the region of interest is displayed on the ultrasound image, the ultrasound apparatus 1000 may display an indicator predetermined corresponding to the region of interest and the view plane at the coordinates of the extracted region of interest. The form of the indicator predetermined corresponding to the region of interest and the view plane may be preset in the ultrasound apparatus 1000.

For example, when the view plane of the ultrasound image is PLAX, the left atrium may be set to be represented by an M mode line; and when the view plane of the ultrasound image is Apical 2 Chamber, the left atrium may be set to be represented by a volume.

The form of the indicator may include a point shape, a line shape, or a box shape but is not limited thereto. Also, the indicator may be represented in a different color from the ultrasound image in order to be discriminated from the ultrasound image.

The point-shaped indicator may be represented in the shape of a point or a small circle at the coordinates of the position of the region of interest in the ultrasound image. Also, the point-shaped indicator may also include direction information of the coordinates of the position of a point with respect to a predetermined position and distance information to the coordinates of the position of the point.

The line-shaped indicator may be represented in the shape of a line segment connecting two coordinate values among the coordinate values of the positions of the region of interest in the ultrasound image. Also, in a sector-shaped ultrasound image, the line-shaped indicator may be represented in the shape of a line segment connecting an apex of the ultrasound image and one coordinate value among the coordinate values of the positions of the region of interest in the ultrasound image. In this case, the line-shaped indicator may also include horizontal direction information or angle information to a predetermined line segment.

The box-shaped indicator may be represented so that that a box includes the region of interest. In this case, the box-shaped indicator may also include coordinate information of a center point of the box, horizontal or vertical length information of the box, or coordinate information of the apex of the box.

The box-shaped indicator may include a color Doppler box and a zoom box. In the color Doppler box, direction information of the speed of the object may be represented by color, and size information of the speed thereof may be represented by brightness. The color Doppler box may be displayed on a B mode image. In the zoom box, the ultrasound image including the region of interest may be represented in an enlarged mode.

Figure 5:
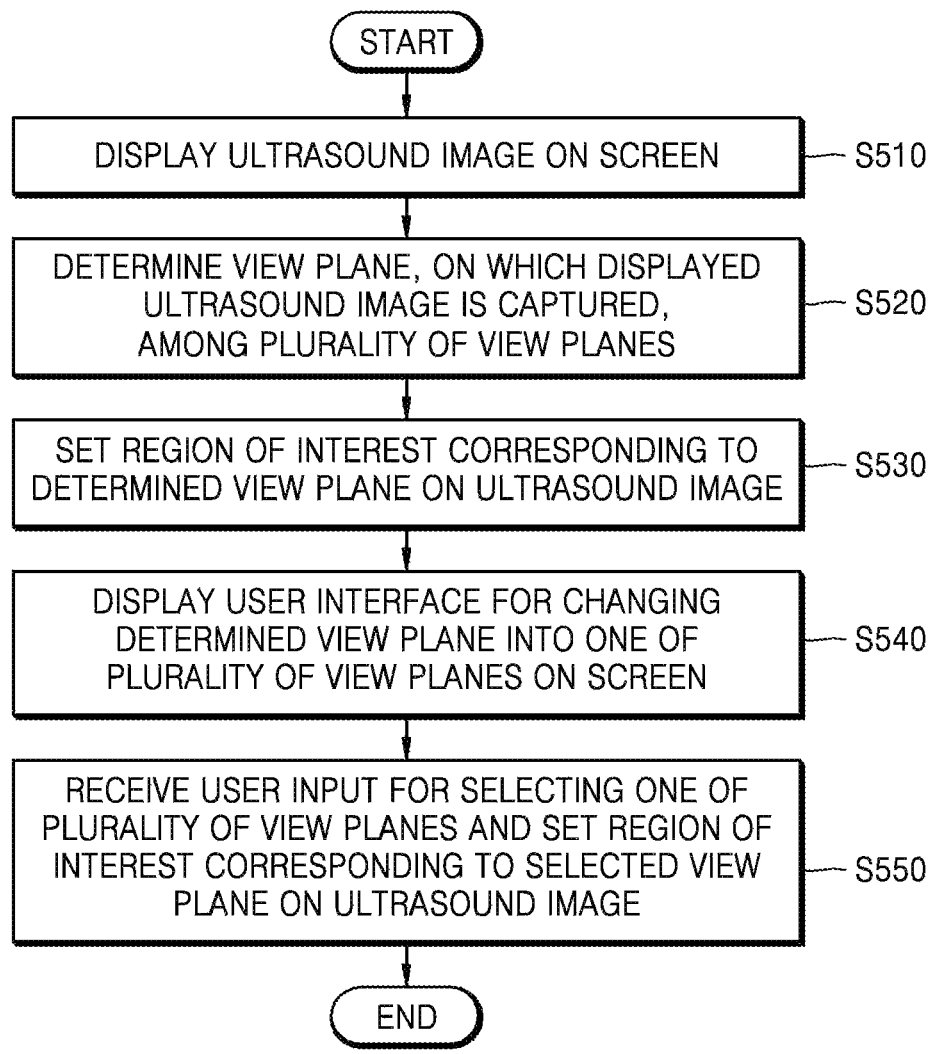
FIG. 5 is a flowchart of a method for changing a view plane of an ultrasound image by an ultrasound apparatus by using a user interface according to an exemplary embodiment.

FIG. 5 is a flowchart of a method for changing a view plane of an ultrasound image by the ultrasound apparatus 1000 by using a user interface according to an exemplary embodiment.

Referring to FIG. 5, in operation S510, the ultrasound apparatus 1000 may display an ultrasound image on the screen. In operation S520, the ultrasound apparatus 1000 may determine a view plane, on which the displayed ultrasound image is captured, among a plurality of view planes. The ultrasound apparatus 1000 may determine the view plane, on which the displayed ultrasound image is captured, by using a classifier that may classify the ultrasound image as one of a plurality of view plane images. In operation S530, the ultrasound apparatus 1000 may set at least one of a plurality of regions of interest corresponding to the determined view plane on the ultrasound image. Operations S510 to S530 may include the features of operations S310 to S330 of FIG. 3.

In operation S540, the ultrasound apparatus 1000 may display a user interface for changing the determined view plane into one of the plurality of view planes on the screen.

The user interface for changing the view plane may include a user interface that may receive a touch input for selecting a plurality of view planes.

Also, the user interface for changing the view plane may be displayed in the screen on which the ultrasound image is displayed. Also, the user interface for changing the view plane may be displayed on an auxiliary display device, not in the screen on which the ultrasound image is displayed.

The user interface for changing the view plane may include a user interface such as a button type, a menu type, a pop-up type, or a dialog type.

Also, the user interface for changing the view plane may include identification information of the plurality of view planes. The display order of the plurality of view planes in the user interface for changing the view plane may be preset in the ultrasound apparatus 1000. The display order of the identification information of the plurality of view planes may be determined based on the similarity to the view plane image determined for the ultrasound image.

The order of the view plane images having similar features with respect to one view plane image may be precalculated and prestored in the ultrasound apparatus 1000 as illustrated in FIG. 6.

FIG. 6 is a diagram illustrating the order of view plane images having similar features with respect to one view plane image according to an exemplary embodiment.

Referring to FIG. 6, when the view plane of the ultrasound image is determined as Apical 2 Chamber, the ultrasound apparatus 1000 may display the identification information of the plurality of view planes in the order of Apical 4 Chamber, Apical 3 Chamber, Mid, RVI, AOR, BAS, APE, SUP, LAX, and IVC in the user interface for changing the view plane.

Accordingly, even when the view plane on which the ultrasound image is actually captured is different from the view plane determined for the ultrasound image by the ultrasound apparatus 1000, the user may quickly change the view plane by displaying the view plane, which is most similar to the determined view plane, at the position that may be first recognized by the user.

Referring to FIG. 5, in operation S550, the ultrasound apparatus 1000 may receive a user input for selecting one of the plurality of view planes and set at least one of a plurality of regions of interest corresponding to the selected view plane on the ultrasound image.

The ultrasound apparatus 1000 may receive a user input for selecting one of the plurality of view planes. For example, the ultrasound apparatus 1000 may receive a touch input for selecting the view plane through the user interface displayed on the screen. Also, the ultrasound apparatus 1000 may receive a user input for selecting one of the plurality of view planes when a button included in a control panel is pressed.

When receiving the user input for selecting one of the plurality of view planes, the ultrasound apparatus 1000 may change the selected view plane into the view plane for the ultrasound image.

Also, the ultrasound apparatus 1000 may acquire information about a preset region of interest corresponding to the view plane for the ultrasound image. The information about the region of interest may include pattern information of the region of interest, display mode information of the region of interest, and position information of the region of interest.

The position and pattern of the same part in each view plane image may be different in each view plane image. Thus, even in the same region of interest, due to a view plane change, the pattern information of the region of interest and the position information of the region of interest may be different.

Also, the ultrasound apparatus 1000 may calculate the coordinates of the position of the region of interest in the ultrasound image. For example, the ultrasound apparatus 1000 may extract the position of a region having a pattern matched with the pattern of the region of interest in the ultrasound image, based on the pattern information of the region of interest. Also, the ultrasound apparatus 1000 may acquire the position of the region of interest in the ultrasound image based on the position information of the region of interest.

The ultrasound apparatus 1000 may set at least one of the plurality of regions of interest corresponding to the view plane on the ultrasound image. The region of interest among the plurality of regions of interest corresponding to the view plane, which will be automatically set on the ultrasound image, may be preset in the ultrasound apparatus 1000 corresponding to the view plane. The region of interest to be automatically set on the ultrasound image corresponding to the view plane may be preset by the user or may be determined based on the usage pattern of the user.

The ultrasound apparatus 1000 may display the region of interest on the ultrasound image, in the form of a point, a line, a box, or the like, based on the calculated coordinates of the region of interest.

Figure 7A:
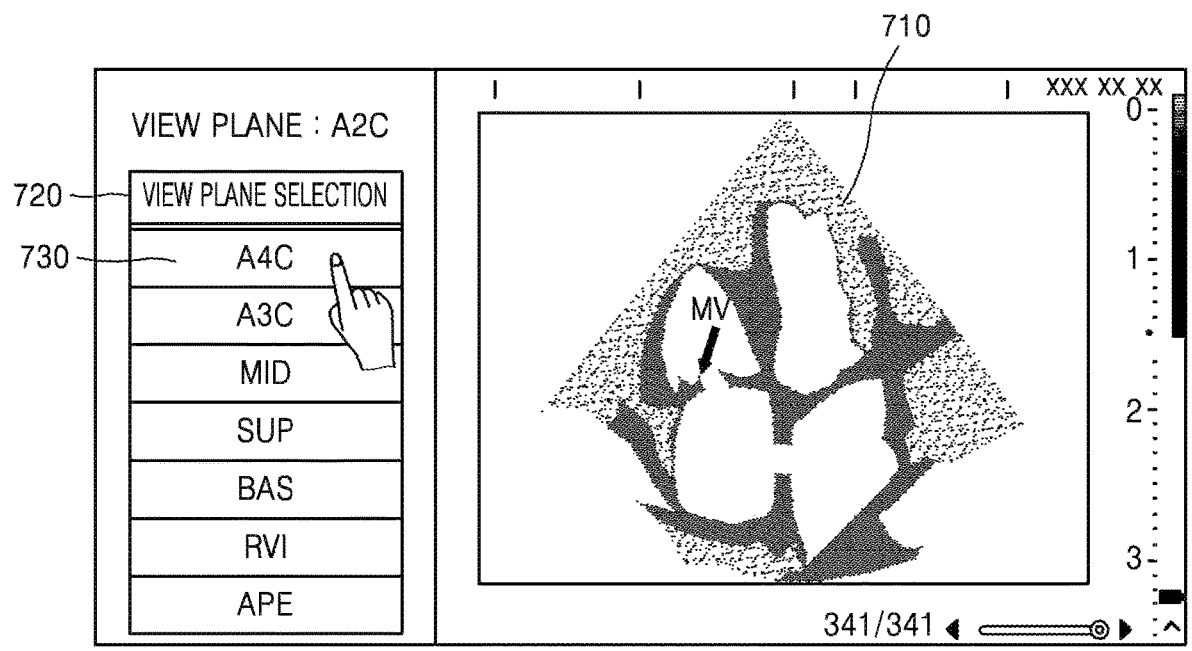
FIGS. 7A and 7B illustrate an example of displaying a user interface for changing a view plane of an ultrasound image by an ultrasound apparatus according to an exemplary embodiment.
Figure 7B:
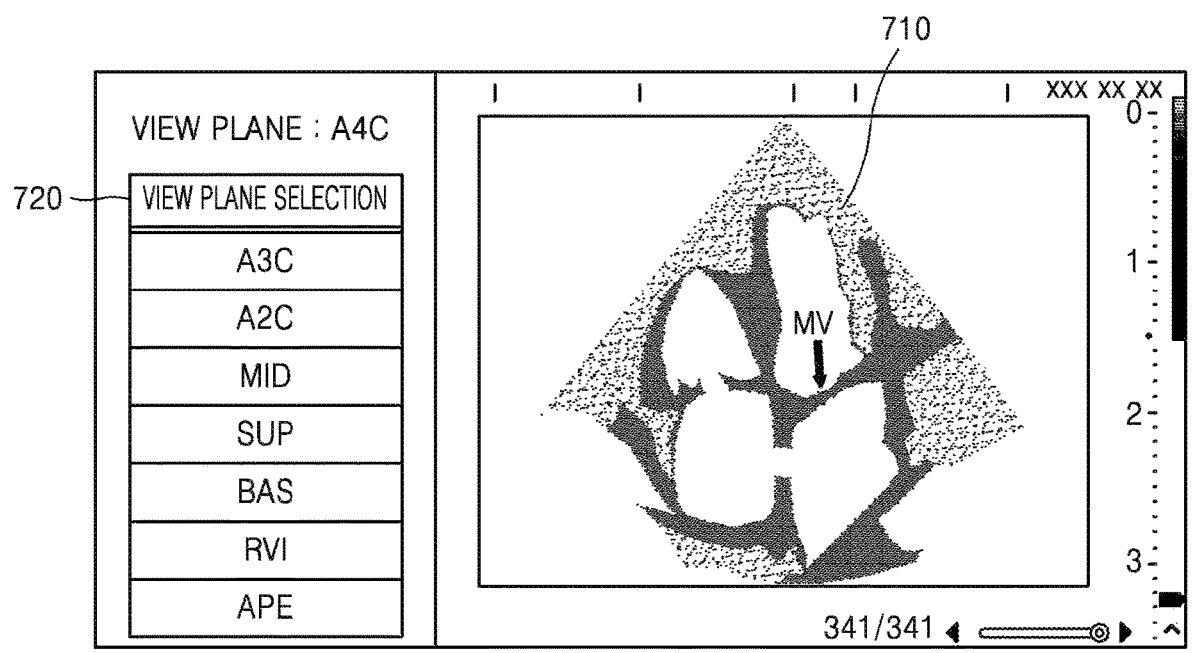

FIGS. 7A and 7B illustrate an example of displaying a user interface for changing a view plane of an ultrasound image by the ultrasound apparatus 1000 according to an exemplary embodiment.

Referring to FIG. 7A, the ultrasound apparatus 1000 may display a captured ultrasound image 710 on the screen. It is assumed that the ultrasound image 710 illustrated in FIG. 7A corresponds to an image of a heart that is captured on an Apical 4 Chamber plane by the user.

The ultrasound apparatus 1000 may determine a view plane of the captured ultrasound image 710. In this case, when the ultrasound image 710 is not clear, the ultrasound apparatus 1000 may determine the view plane of the captured ultrasound image 710 as Apical 2 Chamber.

In this case, the ultrasound apparatus 1000 may extract the position of a mitral valve that is a region of interest preset corresponding to Apical 2 Chamber. For example, the ultrasound apparatus 1000 may acquire pattern, display mode, and position information of the mitral valve that are prestored corresponding to Apical 2 Chamber.

The ultrasound apparatus 1000 may extract the coordinates of the mitral valve on the ultrasound image 710 based on the acquired position and pattern information of the mitral valve. Also, the ultrasound apparatus 1000 may display an indicator representing the mitral valve at the extracted coordinates.

In FIG. 7A, since the view plane determined by the ultrasound apparatus 1000 is Apical 2 Chamber but the view plane, on which the ultrasound image 710 is actually captured, is Apical 4 Chamber, the coordinates of the mitral valve extracted from the ultrasound image 710 may be different from the actual coordinates of the position of the mitral valve.

The ultrasound apparatus 1000 may display a user interface 720 for changing the view plane. The user interface 720 for changing the view plane may be a user interface for selecting one of the plurality of view planes. In this case, the ultrasound apparatus 1000 may acquire the order of the plurality of view planes corresponding to Apical 2 Chamber. Then, the ultrasound apparatus 1000 may display a user interface so that the plurality of view planes may be arranged in the acquired order.

When a user input for selecting Apical 4 Chamber among the plurality of view planes included in the user interface is received (reference numeral 730), the ultrasound apparatus 1000 may change the view plane of the displayed ultrasound image into Apical 4 Chamber.

In this case, the ultrasound apparatus 1000 may extract the position of a mitral valve that is a region of interest preset corresponding to Apical 4 Chamber. For example, the ultrasound apparatus 1000 may acquire pattern, display mode, and position information of the mitral valve that are pre-stored corresponding to Apical 4 Chamber.

The ultrasound apparatus 1000 may extract the coordinates of the mitral valve on the ultrasound image 710 based on the acquired position and pattern of the mitral valve. Also, the ultrasound apparatus 1000 may display an indicator representing the mitral valve.

In this case, since the view plane determined by the ultrasound apparatus 1000 is identical to the view plane on which the ultrasound image is actually captured, the ultrasound apparatus 1000 may extract the accurate position of the mitral valve from the ultrasound image.

Also, the ultrasound apparatus 1000 may display a user interface 720 for changing the view plane. In this case, the ultrasound apparatus 1000 may acquire the order of the plurality of view planes corresponding to Apical 4 Chamber. Then, the ultrasound apparatus 1000 may display a user interface so that the plurality of view planes may be arranged in the acquired order.

Figure 8:
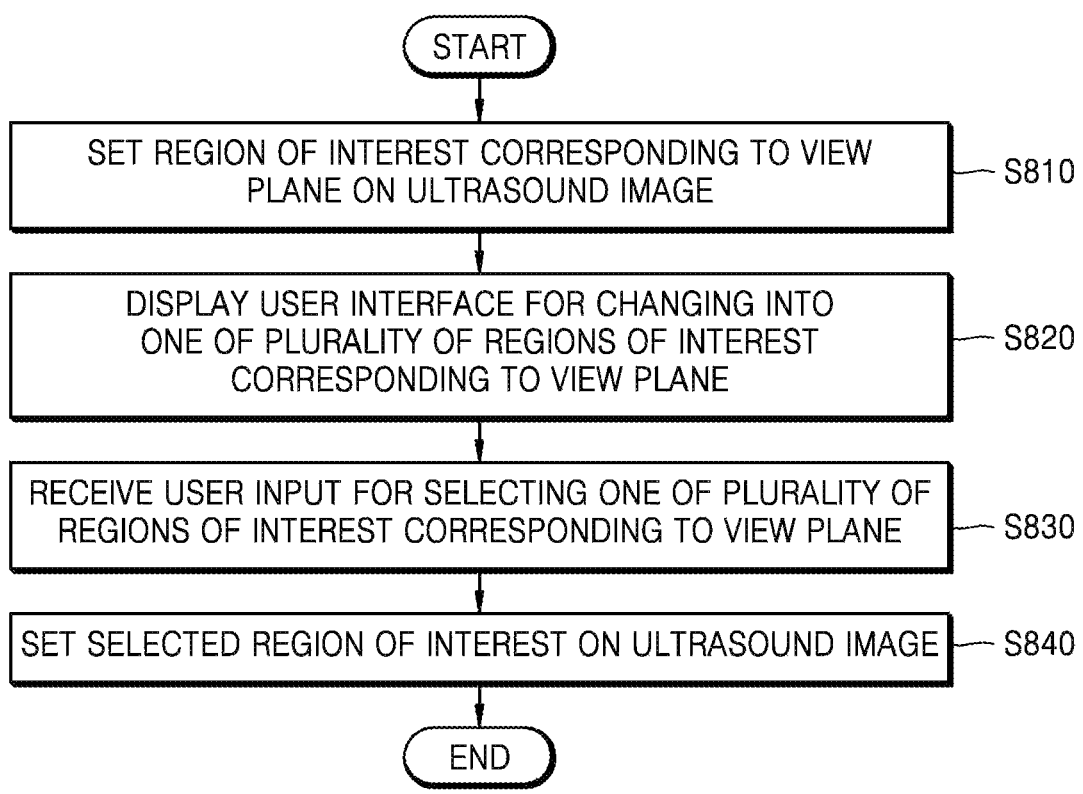
FIG. 8 is a flowchart of a method for changing a region of interest set on an ultrasound image according to an exemplary embodiment.

FIG. 8 is a flowchart of a method for changing a region of interest set on an ultrasound image according to an exemplary embodiment.

Referring to FIG. 8, in operation S810, the ultrasound apparatus 1000 may set at least one region of interest corresponding to the view plane on the ultrasound image.

A plurality of regions of interest to be extracted corresponding to the view plane may be preset in the ultrasound apparatus 1000. Accordingly, the ultrasound apparatus 1000 may acquire information about the plurality of regions of interest to be extracted, based on the determined view plane. The information about the region of interest may include pattern information of the region of interest, display mode information of the region of interest, and position information of the region of interest.

The ultrasound apparatus 1000 may calculate the coordinates of the positions of a plurality of regions of interest in the ultrasound image based on information about the region of interest.

The ultrasound apparatus 1000 may set at least one of the plurality of regions of interest corresponding to the view plane on the ultrasound image. The region of interest among the plurality of regions of interest corresponding to the view plane, which will be automatically set on the ultrasound image, may be preset in the ultrasound apparatus 1000. The region of interest to be automatically set on the ultrasound image may be preset by the user or may be determined based on the usage pattern of the user.

Also, the region of interest to be first measured corresponding to the view plane may be different according to hospitals or users. Accordingly, the ultrasound apparatus 1000 may provide a user interface for setting a region of interest to be automatically set on the ultrasound image after the determination of the view plane.

In operation S820, the ultrasound apparatus 1000 may display a user interface for changing the region of interest into one of the plurality of regions of interest corresponding to the view plane.

The user interface for changing the region of interest may include identification information of the region of interest corresponding to the view plane.

Also, the user interface for changing the region of interest may include a user interface that may receive a touch input for selecting the region of interest.

Also, the user interface for changing the region of interest may be displayed in the screen on which the ultrasound image is displayed. Also, the user interface for changing the region of interest may be displayed on an auxiliary display device, not in the screen on which the ultrasound image is displayed.

The user interface for changing the region of interest may include a user interface such as a button type, a menu type, a pop-up type, or a dialog type.

In operation S830, the ultrasound apparatus 1000 may receive a user input for selecting one of the plurality of regions of interest corresponding to the view plane.

The ultrasound apparatus 1000 may receive a button input or a touch input for selecting the region of interest. Also, the ultrasound apparatus 1000 may receive a drag input from a wheel input device such as a track ball of a control panel, not a touch input or a button input. In this case, the ultrasound apparatus 1000 may select the region of interest according to a drag direction.

Also, the ultrasound apparatus 1000 may receive an input for deleting, adding, or changing the region of interest.

In operation S840, the ultrasound apparatus 1000 may set the selected region of interest on the ultrasound image.

The ultrasound apparatus 1000 may set the selected region of interest on the ultrasound image based on the coordinates of the region of interest extracted in operation S810.

The ultrasound apparatus 1000 may display the set region of interest on the ultrasound image in the form of a point, a line, a box, or the like.

FIGS. 9A, 9B, 9C, and 9D are diagrams illustrating a method for providing a user interface for changing a region of interest according to an exemplary embodiment.

Figure 9A:
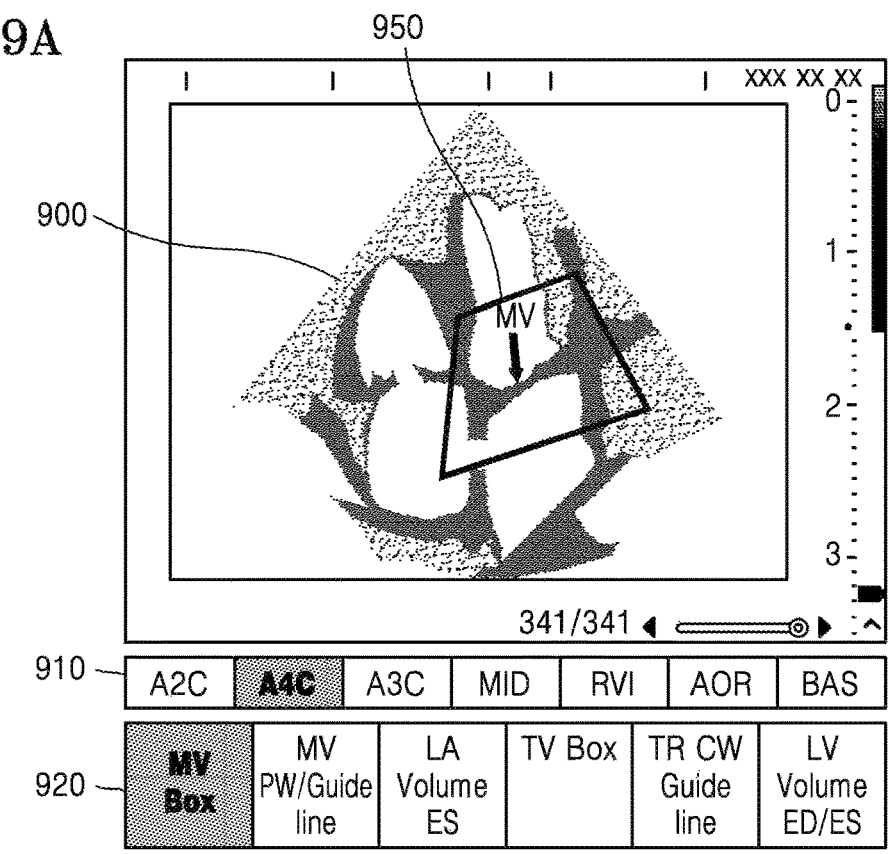
FIGS. 9A, 9B, 9C, and 9D are diagrams illustrating a method for providing a user interface for changing a region of interest according to an exemplary embodiment.

Referring to FIG. 9A, the ultrasound apparatus 1000 may display a user interface 910 for changing the view plane and a user interface 920 for changing the region of interest.

The ultrasound apparatus 1000 may capture an image of a heart of the object on an Apical 4 Chamber plane and display a captured ultrasound image 900 on the screen. Also, the ultrasound apparatus 1000 may classify the captured ultrasound image 900 as an Apical 4 Chamber image. In this case, the ultrasound apparatus 1000 may display an indicator representing the Apical 4 Chamber image on the ultrasound image 900.

Also, the ultrasound apparatus 1000 may acquire information about a region of interest predetermined corresponding to the Apical 4 Chamber image. Corresponding to the Apical 4 Chamber image, a mitral valve, a right tricuspid valve, a left atrium, a tricuspid valve, or a left ventricle may be predetermined as the region of interest in the ultrasound apparatus 1000. Accordingly, the ultrasound apparatus 1000 may extract pattern information, display mode information, and position information of the mitral valve, the right tricuspid valve, the left atrium, the tricuspid valve, or the left ventricle corresponding to the Apical 4 Chamber image.

Accordingly, the ultrasound apparatus 1000 may display a user interface 920 for selecting the mitral valve, the right tricuspid valve, the left atrium, the tricuspid valve, or the left ventricle.

Also, the ultrasound apparatus 1000 may extract the coordinates of the region of interest from the ultrasound image 900 based on the position information of the region of interest. For example, the ultrasound apparatus 1000 may acquire the coordinates of the mitral valve in the ultrasound image 900 from the position information of the mitral valve. Also, the ultrasound apparatus 1000 may extract the coordinates of a region matched with the pattern of the mitral valve in the ultrasound image 900 based on the pattern information of the mitral valve. The ultrasound apparatus 1000 may extract the coordinates of the right tricuspid valve, the left atrium, the tricuspid valve, or the left ventricle from the ultrasound image 900.

Also, in the ultrasound apparatus 1000, MV Box among the plurality of regions of interest corresponding to Apical 4 Chamber may be preset to be automatically set on the ultrasound image 900. Accordingly, the ultrasound apparatus 1000 may display a box-shaped indicator 950 at the coordinates of the mitral valve.

Figure 9B:
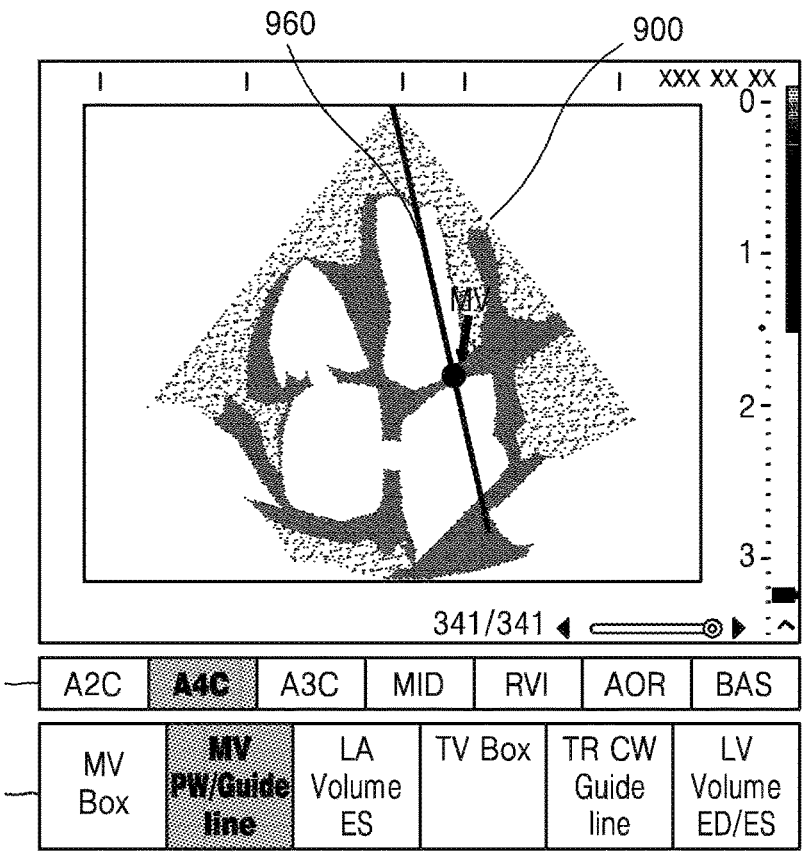

Referring to FIG. 9B, when receiving a user input for changing the region of interest on the ultrasound image 900 into a mitral valve guide line (MV PW/Guide Line), the ultrasound apparatus 1000 may delete a mitral valve box and display a line segment 960 connecting an apex of the ultrasound image 900 and the mitral valve.

Figure 9C:
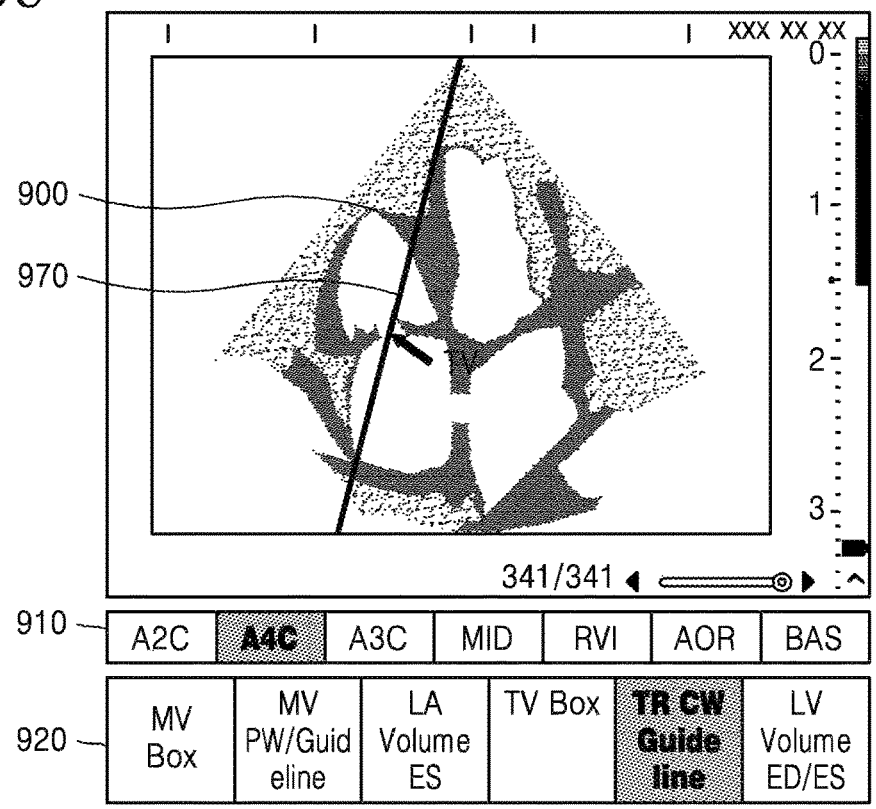

Referring to FIG. 9C, when receiving a user input for changing the region of interest on the ultrasound image 900 into a right tricuspid valve guide line (TR CW Guide Line), the ultrasound apparatus 1000 may release the region of interest set on the mitral valve and set the right tricuspid valve as the region of interest. In this case, the ultrasound apparatus 1000 may display a line segment 970 connecting an apex of the ultrasound image 900 and the right tricuspid valve by using the extracted coordinates of the right tricuspid valve.

Figure 9D:
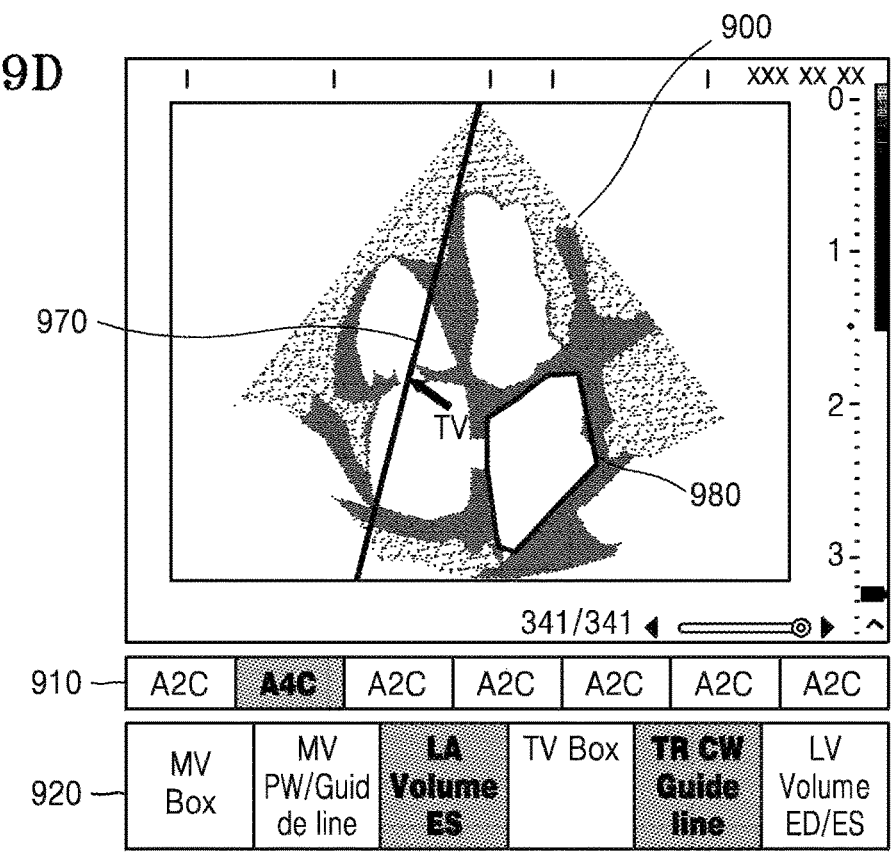

Referring to FIG. 9D, when receiving a user input for adding a left atrium (LA) on the ultrasound image 900, the ultrasound apparatus 1000 may set the left atrium as the region of interest. In this case, the ultrasound apparatus 1000 may display a closed curve 980 surrounding the left atrium by using the extracted coordinates of the left atrium.

FIG. 10 is a flowchart of a method for determining a classifier according to an exemplary embodiment.

Referring to FIG. 10, in operation S1010, the ultrasound apparatus 1000 may collect sample data for generating a classifier. In operation S1020, the ultrasound apparatus 1000 may change a plurality of ultrasound images captured in operation S1010 into the same format. In operation S1030, the ultrasound apparatus 1000 may determine a pattern for discriminating a plurality of view planes. In operation S1040, the ultrasound apparatus 1000 may extract the features of the pattern determined in operation S1030. Operations S1010 to S1040 may include the features of operations S210 to S240 of FIG. 2.

In operation S1050, the ultrasound apparatus 1000 may model a plurality of classifiers for classifying an ultrasound image as one of two view plane images, based on the features of the pattern determined in operation S1040.

The ultrasound apparatus 1000 may determine a plurality of classifiers for classifying the ultrasound image as two view plane images of different combinations among a plurality of view plane images. For example, when the ultrasound image is to be classified into A, B, C, D, and E, the ultrasound apparatus 1000 may determine 10 classifiers for classifying the ultrasound image into A and B, A and C, A and D, A and E, B and C, B and D, B and E, C and D, C and E, and D and E. Thus, when the ultrasound image is to be classified into N view plane images, the ultrasound apparatus 1000 may determine $(N^2-N)/2$ classifiers.

Also, when determining a classifier for classifying the ultrasound image as one of view plane images A and B, the ultrasound apparatus 1000 may generate a mathematical model of the classifier so that the ultrasound image may be classified as the view plane image A or B having more similar features to the features extracted from the ultrasound image. The mathematical model of the classifier may be generated by various methods that are available in the technical field of the inventive concept.

In operation S1060, the ultrasound apparatus 1000 may test the classifier generated in operation S1050 by a plurality of ultrasound images and adjust a coefficient of the mathematical model of the classifier.

The ultrasound apparatus 1000 may set an ultrasound image, of which the view plane is identified, as an input value of the classifier and determine whether an output value of the classifier represents the identified view plane. The ultrasound apparatus 1000 may adjust the coefficient of the mathematical model of the classifier based on whether the output value of the classifier represents the identified view plane. A method for classifying the ultrasound image as one view plane image by the ultrasound apparatus 1000 by using the classifier will be described below with reference to FIGS. 11 to 13.

The ultrasound apparatus 1000 may determine the mathematical model so that the classifier may represent a minimum error, by performing a test on the classifier with respect to a plurality of ultrasound images whose view plane is identified.

As the number of view plane images to be considered by the classifier increases, the classification accuracy may decrease. Thus, by restricting the number of view planes to be considered by the classifier to "2", the classification accuracy may be increased.

Also, the number of view planes to be considered by the classifier decreases, the number of patterns necessary for discriminating the view planes or the number of features to be extracted from the patterns may decrease.

As the number of patterns or features decreases, the calculation amount may exponentially decrease. Thus, by restricting the number of view planes to be considered by the classifier to "2", the calculation amount and the calculation complexity may be decreased and the classification time may be decreased.

FIGS. 11A and 11B illustrate a method for determining a view plane of an ultrasound image by using a classifier according to an exemplary embodiment.

Referring to FIG. 11A, the ultrasound apparatus 1000 may classify the ultrasound image as one of 11 view plane images. It is assumed that each view plane image has a pattern discriminated from the patterns of other view plane images.

The ultrasound apparatus 1000 may classify the ultrasound image by using the plurality of classifiers determined in FIG. 10. That is, in order to classify the ultrasound image as one of 11 view plane images, the ultrasound apparatus 1000 may generate 55 classifiers for classifying the ultrasound image into two view plane images of different combinations. Accordingly, the class of one classifier may be two view plane images.

Referring to FIG. 11B, the ultrasound apparatus 1000 may classify the ultrasound image as one of 11 view plane images.

The ultrasound apparatus 1000 may extract features from an input ultrasound image. For example, the ultrasound apparatus 1000 may extract a predetermined patch block region from the input ultrasound image and extract the features of ultrasound image data constituting a patch block.

In a first operation S1110, the ultrasound apparatus 1000 may select one of 55 classifiers and classify the ultrasound image as one view plane image. For example, the ultrasound apparatus 1000 may select a classifier for classifying the ultrasound image into a PLAX image and an RV Inflow image. Then, the classifier may select the PLAX image as the view plane image having more similar features to the features extracted from the ultrasound image.

In a second operation S1120, the ultrasound apparatus 1000 may select one of remaining 9 view plane images among 11 view plane images (except the PLAX image and the RV Inflow image) and select a classifier for classifying the selected view plane image and the PLAX image determined in the first operation S1110. For example, the ultrasound apparatus 1000 may select SAX-AV among 9 view plane images except the PLAX image and the RV Inflow image. Then, the ultrasound apparatus 1000 may select a classifier for classifying the ultrasound image as one of the PLAX image and the SAX-AV image. Then, the classifier may select the SAX-AV image as the view plane image having more similar features to the features of the ultrasound image.

In a third operation S1130, the ultrasound apparatus 1000 may select one of remaining 8 view plane images among 11 view plane images (except the PLAX image, the RV Inflow image, and the SAX-AV image) and select a classifier for classifying the selected view plane image and the SAX-AV image determined in the second operation S1120. For example, the ultrasound apparatus 1000 may select a Suprasternal image among 8 view plane images except the PLAX image, the RV Inflow image, and the SAX-AV image and classify the ultrasound image as one of the SAX-AV image and the Suprasternal image by using a classifier for classifying the SAX-AV image and the Suprasternal image. In this case, the classifier may select the SAX-AV image as the view plane image having more similar features to the features of the ultrasound image.

Likewise, by continuing to select a classifier to classify the ultrasound image as one of two view plane images, in a last operation S1140, the ultrasound apparatus 1000 may select a classifier for classifying the view plane image determined in the previous operation and the last view plane image that is not compared among 11 view plane images. For example, the ultrasound apparatus 1000 may classify the ultrasound image as one of Apical 3/5 chamber and Apical 4 Chamber by using a classifier for classifying the Apical 3/5 chamber image determined in the previous operation and the Apical 4 Chamber image that is the last view plane image. In this case, the classifier may select the Apical 4 Chamber image as the view plane image having more similar features to the features of the ultrasound image.

Accordingly, the ultrasound apparatus 1000 may determine that the input ultrasound image is captured on the Apical 4 Chamber plane.

FIGS. 12A to 12C illustrate a method for determining a view plane of an ultrasound image by using a classifier according to another exemplary embodiment.

Referring to FIG. 12A, the ultrasound apparatus 1000 may classify the ultrasound image as one of 5 view plane images. Also, the ultrasound apparatus 1000 may include 10 classifiers for classifying the ultrasound image as one of 5 view plane images.

The ultrasound apparatus 1000 may input the ultrasound image into all classifiers and add a score to the view plane image selected by the classifier.

Referring to FIG. 12B, the ultrasound apparatus 1000 may input the ultrasound image into a classifier for classifying the ultrasound image into an Apical 2 Chamber image and an Apical 4 Chamber image and add "1" to the score of the Apical 2 Chamber image when the result value of the classifier is the Apical 2 Chamber image. Likewise, the ultrasound apparatus 1000 may input the ultrasound image into all classifiers and add "1" to the score of the view plane image selected by the classifier.

The ultrasound apparatus 1000 may determine the view plane, on which the ultrasound image is captured, based on the view plane image having the highest score.

Referring to FIG. 12C, since Apical 2 Chamber has the highest score, the ultrasound apparatus 1000 may determine the view plane, on which the ultrasound image is captured, as Apical 2 Chamber.

FIGS. 13A to 13D illustrate a method for determining a view plane of an ultrasound image by using a classifier according to another exemplary embodiment.

Referring to FIG. 13A, the ultrasound apparatus 1000 may classify the ultrasound image as one of 5 view plane images. Also, the ultrasound apparatus 1000 may include 10 classifiers for classifying the ultrasound image as one of 5 view plane images.

When the ultrasound image is classified as one of N view plane images, the ultrasound apparatus 1000 may assume the input ultrasound image to be one of N view plane images. Then, the ultrasound apparatus 1000 may select (N−1) classifiers for classifying the assumed view plane image and the (N−1) view plane images other than the assumed view plane image. Then, the ultrasound apparatus 1000 may input the ultrasound image into the selected (N−1) classifiers and determine whether the result value of the classifier represents the assumed view plane image. Then, when the (N−1) classifiers select the assumed view plane images more than a reference ratio, the ultrasound apparatus 1000 may determine the assumed view plane image as the view plane image of the ultrasound image. Accordingly, the ultrasound apparatus 1000 may determine a view plane on which the ultrasound image is captured.

When the (N−1) classifiers do not select the assumed view plane images more than the reference ratio, the ultrasound apparatus 1000 may assume the ultrasound image to be one of the (N−1) view plane images except the first assumed view plane image. Then, the ultrasound apparatus 1000 may select (N−2) classifiers for classifying the second assumed view plane image and the (N−2) view plane images other than the second assumed view plane image. Then, the ultrasound apparatus 1000 may input the ultrasound image into the selected (N−2) classifiers and determine whether the result value of the classifier represents the second assumed view plane image. Then, when the (N−2) classifiers select the second assumed view plane image more than a reference ratio, the ultrasound apparatus 1000 may determine the second assumed view plane image as the view plane image of the ultrasound image.

When the (N−2) classifiers do not select the second assumed view plane image more than the reference ratio, the ultrasound apparatus 1000 may identify the result value by selecting (N−3) classifiers in the same way as above. The ultrasound apparatus 1000 may continue to perform the same method until the assumed view plane image is selected more than the reference ratio.

Referring to FIG. 13B, the ultrasound apparatus 1000 may assume the ultrasound image to be an Apical 2 Chamber image among 5 view plane images. Then, the ultrasound apparatus 1000 may select 4 classifiers for classifying the Apical 2 Chamber image and each of the other four view plane images except the Apical 2 Chamber image. Then, the ultrasound apparatus 1000 may input the ultrasound image into the selected 4 classifiers and determine whether the result value of the classifier represents the Apical 2 Chamber image.

When only one of the 4 classifiers classifies the ultrasound image as the Apical 2 Chamber image, the ultrasound apparatus 1000 may determine that the ultrasound image does not correspond to the Apical 2 Chamber image.

Referring to FIG. 13C, the ultrasound apparatus 1000 may assume the ultrasound image to be an Apical 3 Chamber image among 4 view plane images except the Apical 2 Chamber image.

Then, the ultrasound apparatus 1000 may select 3 classifiers for classifying the Apical 3 Chamber image and each of the other 3 view plane images except the Apical 3 Chamber image among the other 4 view plane images. Then, the ultrasound apparatus 1000 may input the ultrasound image into the selected 3 classifiers and determine whether the result value of the classifier represents the Apical 3 Chamber image.

When only one of the 3 classifiers classifies the ultrasound image as the Apical 3 Chamber image, the ultrasound apparatus 1000 may determine that the ultrasound image does not correspond to the Apical 3 Chamber image.

Referring to FIG. 13D, the ultrasound apparatus 1000 may assume the ultrasound image to be an Apical 4 Chamber image among 3 view plane images except the Apical 2 Chamber image and the Apical 3 Chamber image.

Then, the ultrasound apparatus 1000 may select 2 classifiers for classifying the Apical 4 Chamber image and each of the other 2 view plane images except the Apical 4 Chamber image among the other 3 view plane images. Then, the ultrasound apparatus 1000 may input the ultrasound image into the selected 2 classifiers and determine whether the result value of the classifier represents the Apical 4 Chamber image.

When both of the 2 classifiers classify the ultrasound image as the Apical 4 Chamber image, the ultrasound apparatus 1000 may determine that the ultrasound image corresponds to the Apical 4 Chamber image. Accordingly, the ultrasound apparatus 1000 may determine that the ultrasound image is captured on the Apical 4 Chamber plane.

FIG. 14 is a flowchart of a method for determining a classifier according to an exemplary embodiment.

Referring to FIG. 14, in operation S1410, the ultrasound apparatus 1000 may collect sample data for generating a classifier. In operation S1420, the ultrasound apparatus 1000 may change a plurality of ultrasound images captured in operation S1410 into the same format. Operations S1410 to S1420 may include the features of operations S210 to S240 of FIG. 2.

In operation S1430, the ultrasound apparatus 1000 may define two view plane images of similar patterns as one view plane image.

For example, among the view planes, a basal plane and a midplane have similar patterns such that they are difficult to discriminate with the naked eye. The ultrasound apparatus 1000 may extract the features of the view plane images and define the view plane images, which have features more similar than a predetermined criterion, as one view plane image. In this case, the ultrasound apparatus 1000 may define the basal plane and the mid plane as one view plane.

Thus, when the ultrasound image is to be classified into A, B, C, D, and E, if patterns A and B are similar to each other, the ultrasound apparatus 1000 may assume the A and B to be one view plane and may adjust AB, C, D, and E to view plane class.

In operation S1440, the ultrasound apparatus 1000 may determine a plurality of patterns for classifying two view planes of different combinations among a plurality of view planes.

When the ultrasound image is to be classified into AB, C, D, and E view plane images, the ultrasound apparatus 1000 may determine a pattern for each of view plane combinations of AB and C, AB and D, AB and E, C and D, C and E, and D and E.

In operation S1450, the ultrasound apparatus 1000 may determine a pattern for classifying 2 view plane images defined as one view plane image.

The ultrasound apparatus 1000 may determine a pattern for classifying A and B view plane images defined as one view plane image in operation S1430.

In operation S1460, the ultrasound apparatus 1000 may extract the features of the pattern determined in operations S1440 and S1450.

For example, the features may include a ranklet of the pattern, an average value, an edge histogram, an 8×8 resize image, and an homogeneity calculation value. Since the meanings of these terms may be easily understood by those of ordinary skill in the art, detailed descriptions thereof will be omitted herein.

In operation S1470, the ultrasound apparatus 1000 may model a plurality of classifiers for classifying an ultrasound image as one of two view plane images, based on the features of the pattern determined in operation S1460.

The ultrasound apparatus 1000 may determine a plurality of classifiers for classifying the ultrasound image as two view plane images of different combinations among a plurality of view plane images. For example, when the ultrasound image is to be classified into A, B, C, D, and E and view plane images A and B are similar to each other, the ultrasound apparatus 1000 may determine a plurality of classifiers for classifying the ultrasound image into AB and C, AB and D, AB and E, C and D, C and E, D and E, and A and B.

In operation S1480, the ultrasound apparatus 1000 may test the classifier generated in operation S1470 by a plurality of ultrasound images and adjust a coefficient of a mathematical model of the classifier.

FIGS. 15A to 15C illustrate an example of a method for determining a view plane of an ultrasound image by using a classifier according to another exemplary embodiment.

Referring to FIG. 15A, the ultrasound apparatus 1000 may classify the ultrasound image as one of 11 view plane images. Among them, an SAX-Basal image and an SAX-Mid image may have similar patterns. Accordingly, the ultrasound apparatus 1000 may determine the SAX-Basal image and the SAX-Mid image as one view plane image (SAX-Basal/Mid). The SAX-Basal/Mid image may refer to a view plane image having the common pattern of the SAX-Basal image and the SAX-Mid image.

Referring to FIG. 15B, the ultrasound apparatus 1000 may classify the ultrasound image as one of 10 view plane images obtained by replacing the SAX-Basal image and the SAX-Mid image with the SAX-Basal/Mid image in the 11 view plane images.

The ultrasound apparatus 1000 may classify the ultrasound image as one view plane image in the same way as described above. In order to classify the ultrasound image as one of 10 view plane images, the ultrasound apparatus 1000 may generate 45 classifiers for classifying the ultrasound image into 2 view plane images of different combinations.

The ultrasound apparatus 1000 may extract features from an input ultrasound image. For example, the ultrasound apparatus 1000 may extract a predetermined patch block region from the input ultrasound image and extract the features of ultrasound image data constituting a patch block.

In a first operation S1510, the ultrasound apparatus 1000 may select one of 45 classifiers and classify the ultrasound image as one view plane image. For example, the ultrasound apparatus 1000 may select a classifier for classifying the ultrasound image into a PLAX image and an RV Inflow image. Then, the classifier may select the PLAX image as the view plane image having more similar features to the features extracted from the ultrasound image.

In a second operation S1520, the ultrasound apparatus 1000 may select one of 8 view plane images among 10 view plane images (except the PLAX image and the RV Inflow image) and select a classifier for classifying the selected view plane image and the PLAX image determined in the first operation S1510. For example, the ultrasound apparatus 1000 may select an SAX-AV image among 8 view plane images except the PLAX image and the RV Inflow image. Then, the classifier may select the SAX-AV image as the view plane image having more similar features to the features of the ultrasound image.

In a third operation S1530, the ultrasound apparatus 1000 may select one of 7 view plane images among 10 view plane images (except the PLAX image, the RV Inflow image, and the SAX-AV image) and select a classifier for classifying the selected view plane image and the SAX-AV image determined in the second operation S1520. For example, the ultrasound apparatus 1000 may select a Suprasternal image among 7 view plane images except the PLAX image, the RV Inflow image, and the SAX-AV image and classify the ultrasound image as one of the SAX-AV image and the Suprasternal image by using a classifier for classifying the SAX-AV image and the Suprasternal image. In this case, the classifier may select the SAX-AV image as the view plane image having more similar features to the features of the ultrasound image.

Likewise, by continuing to select a classifier to classify the ultrasound image as one of two view plane images, in a last operation S1540, the ultrasound apparatus 1000 may select a classifier for classifying the view plane image determined in the previous operation and the last view plane image that is not compared among 10 view plane images. For example, the ultrasound apparatus 1000 may classify the ultrasound image as one of SAX-Basal/Mid and Apical 4 Chamber by using a classifier for classifying the SAX-Basal/Mid image determined in the previous operation and the Apical 4 Chamber image that is the last view plane image. In this case, the classifier may select the SAX-Basal/Mid image as the view plane image having more similar features to the features of the ultrasound image.

Also, although not illustrated in the drawings, in the same way as illustrated in FIG. 12 or 13, the ultrasound apparatus 1000 may classify the ultrasound image as one of 10 view plane images obtained by replacing the SAX-Basal image and the SAX-Mid image with the SAX-Basal/Mid image.

When the SAX-Basal/Mid image is determined as the view plane image of the ultrasound image, the ultrasound apparatus 1000 may classify the ultrasound image as one of the SAX-Basal image and the SAX-Mid image by using a classifier having the class of the SAX-Basal image and the SAX-Mid image.

Referring to FIG. 15C, the classifier may select the SAX-Mid image as the view plane image having more similar features to the features of the ultrasound image.

Accordingly, the ultrasound apparatus 1000 may determine that the input ultrasound image is captured on the SAX-Mid plane.

Figure 16:
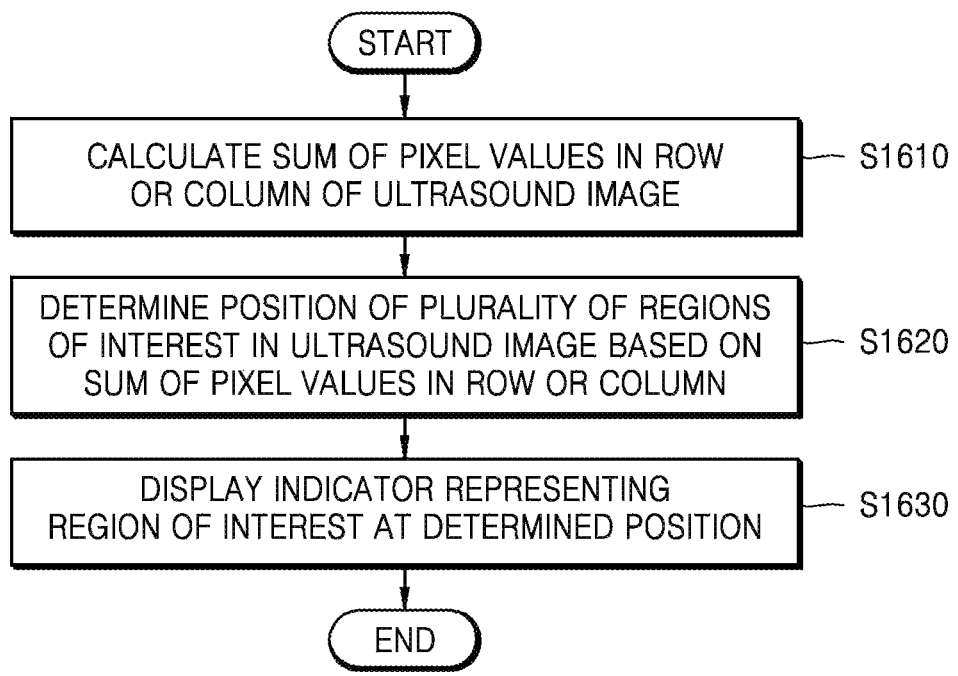
FIG. 16 is a flowchart of a method for detecting the position of a region of interest in an ultrasound image and displaying the same by an ultrasound apparatus according to an exemplary embodiment.

FIG. 16 is a flowchart of a method for detecting the position of a region of interest in an ultrasound image and displaying the same by the ultrasound apparatus 1000 according to an exemplary embodiment.

Referring to FIG. 16, in operation S1610, the ultrasound apparatus 1000 may calculate the sum of pixel values in a row or a column of the ultrasound image.

For example, the ultrasound apparatus 1000 may calculate the sum of the respective pixel values in the row of the ultrasound image or the sum of the respective pixel values in the column of the ultrasound image. Hereinafter, a method for calculating the sum of the respective pixel values in the row of the ultrasound image or the sum of the respective pixel values in the column of the ultrasound image will be referred to as a projection method.

The ultrasound apparatus 1000 may perform projection on the ultrasound image displayed on the screen of the ultrasound apparatus 1000. That is, the ultrasound apparatus 1000 may generate a scan line based on an ultrasound signal received from the object, scan-converting the generated scan line, and then perform projection on the ultrasound image. Also, the ultrasound apparatus 1000 may perform projection on the scan line prior to the scan-conversion Also, the ultrasound apparatus 1000 may perform projection on an average image of a plurality of consecutive frames.

The ultrasound apparatus 1000 may calculate the brightness value of the ultrasound image corresponding to the coordinates of each row or column by calculating the sum of pixel values in each row or column of the ultrasound image. Also, the ultrasound apparatus 1000 may generate a function for determining the brightness value of the ultrasound image corresponding to the coordinate value of each row or column.

In operation S1620, the ultrasound apparatus 1000 may determine the position of the plurality of regions of interest in the ultrasound image based on the sum of the pixel values in the row or the column of the ultrasound image.

The ultrasound apparatus 1000 may transmit an ultrasound signal to the object and receive an ultrasound signal reflected from the object. In this case, since the ultrasound apparatus 1000 generates the ultrasound image by varying the pixel value according to the strength of the received ultrasound signal, the row or column having a high pixel value in the ultrasound image may be the display position of an organic of the object.

Accordingly, the ultrasound apparatus 1000 may determine the position of the row or column, which the sum of the pixel values is greater than or equal to a reference value, as the display position of the organ of the object. In this case, the organ displayed in the ultrasound image may be determined based on a predetermined view plane. For example, when the Apical 4 Chamber image is projected on the vertical direction, the ultrasound apparatus 1000 may determine three regions having the high sum of pixel values in each column of the Apical 4 Chamber image as a right heart wall, a diaphragm, and a left heart wall.

Also, the ultrasound apparatus 1000 may determine the position of a plurality of regions of interest corresponding to the view plane based on the detected position of the organ. The plurality of regions of interest may be preset corresponding to the view plane. For example, in the ultrasound apparatus 1000, corresponding to the Apical 4 Chamber image, a mitral valve (MV) sample volume, a tricuspid valve (TV) sample volume, and a pulmonary vein (PV) sample volume may be set as the region of interest.

When Apical 4 Chamber is determined as the view plane, the ultrasound apparatus 1000 may detect the position of the MV sample volume, the TV sample volume, and the PV sample volume based on the detected position of the organ.

In operation S1630, the ultrasound apparatus 1000 may display an indicator representing at least one of the plurality of regions of interest at the determined position.

The indicator may be set in the ultrasound apparatus 1000, corresponding to the region of interest and the view plane. For example, an MV zoom box may be set corresponding to the MV sample volume of the Apical 4 Chamber image. Accordingly, the ultrasound apparatus 1000 may display the MV zoom box at the position of the MV sample volume detected in operation S1620.

Figure 17:
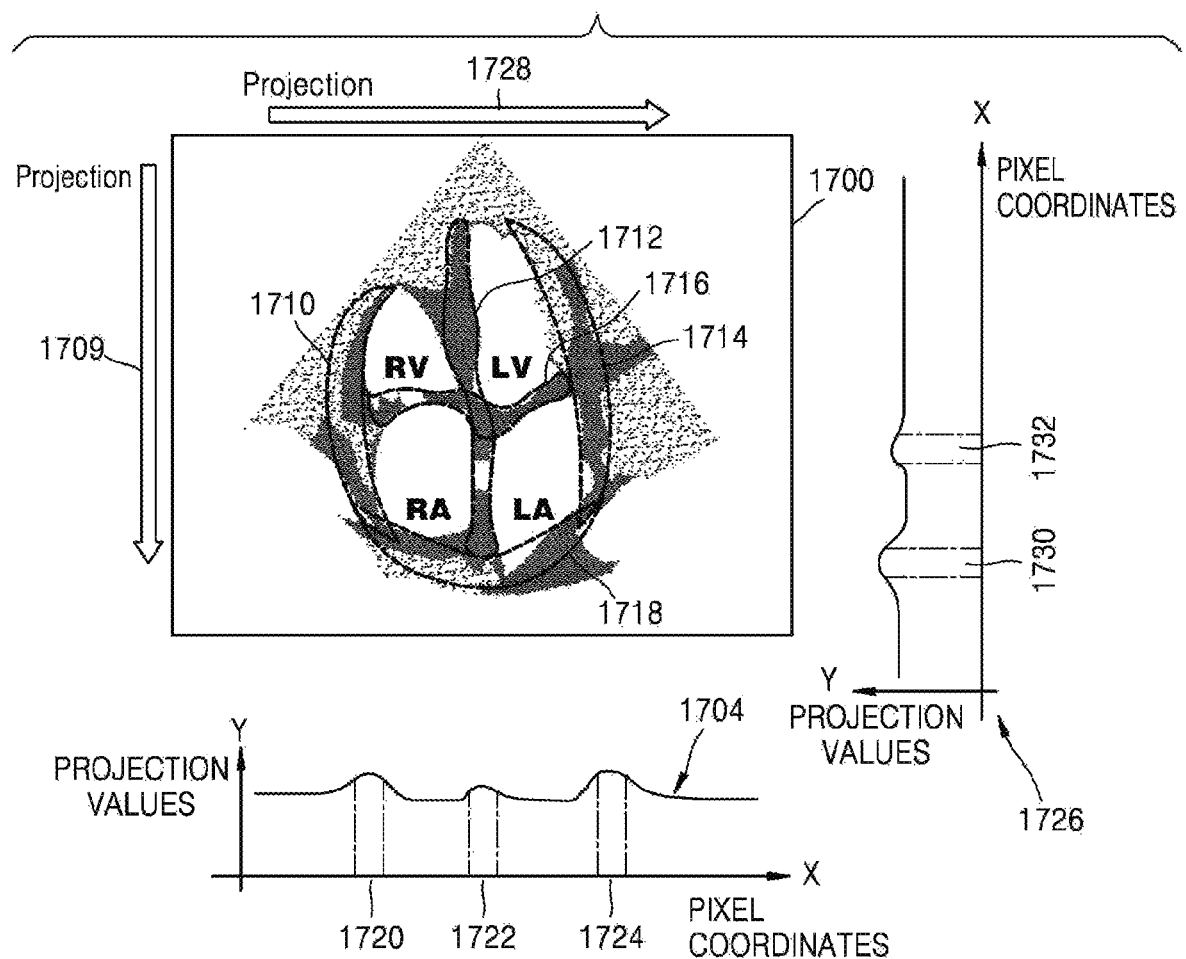
FIG. 17 illustrates an example of a method for detecting the boundary of a heart in an Apical 4 Chamber image according to an exemplary embodiment.

FIG. 17 illustrates an example of a method for detecting the boundary of a heart in an Apical 4 Chamber image according to an exemplary embodiment.

As illustrated in graph 1700, an Apical 4 Chamber image may be an ultrasound image in which a right ventricle (RV) is located on a left top, a left ventricle (LV) is located on a right top, a right atrium (RA) is located at a left bottom, and a left atrium (LA) is located at a right bottom.

Referring to FIG. 17, the ultrasound apparatus 1000 may calculate the sum of pixel values in each column of the Apical 4 Chamber image. Also, the ultrasound apparatus 1000 may generate a vertical projection function 1709 for determining the sum of pixel values in each column (graph 1704). In the vertical projection function, an X axis may represent the coordinates of horizontal pixels of the ultrasound image. Also, in the vertical projection function, a Y axis may represent the sum of pixel values in each column.

Since the Apical 4 Chamber image may be an image in which a right heart wall and a left heart wall are located horizontally with the center of a diaphragm, the ultrasound apparatus 1000 may detect three regions representing a right heart wall 1710, a diaphragm 1712, and a left heart wall 1714 in the vertical projection function. For example, in the vertical projection function, the ultrasound apparatus 1000 may determine the pixel coordinates of three regions having a high projection value as the positions of the right heart wall 1710, the diaphragm 1712, and the left heart wall 1714. The ultrasound apparatus 1000 may detect the pixel coordinates of a first region 1720 as the position of the right heart wall 1710, the pixel coordinates of a second region 1722 as the position of the diaphragm 1712, and the pixel coordinates of a fourth region 1724 as the position of the left heart wall 1714.

Referring to FIG. 17, the ultrasound apparatus 1000 may calculate the sum of pixel values in each row of the Apical 4 Chamber image (graph 1726). Also, the ultrasound apparatus 1000 may generate a horizontal projection function 1728 for determining the sum of pixel values in each row. In the horizontal projection function, an X axis may represent the coordinates of vertical pixels of the ultrasound image. Also, in the horizontal projection function, a Y axis may represent the sum of pixel values in each row.

In the case of the Apical 4 Chamber image, since a bottom boundary 1718 of the atrium is represented bright in a lower region of the ultrasound image and heart valves 1716 (Tricuspid valve and mitral valve) are located in a line at the center of the ultrasound image, the ultrasound apparatus 1000 may detect two regions representing the bottom boundary 1718 of the atrium and the valve 1716 in the horizontal projection function. For example, the ultrasound apparatus 1000 may detect the pixel coordinates of a first region 1730 as the position of the bottom boundary 1718 of the atrium, and the pixel coordinates of a second region 1732 as the position of the valve 1716.

By detecting the position of the boundary of the heart, the ultrasound apparatus 1000 may determine four regions on the ultrasound image based on three horizontal region coordinates 1720, 1722, and 1724 and two vertical region coordinates 1730 and 1732. The ultrasound apparatus 1000 may determine, among the determined four regions, the left top as the left ventricle (LV), the right top as the right ventricle (RV), the left bottom as the left atrium (LA), and the right bottom as the right atrium (RA).

Figure 18:
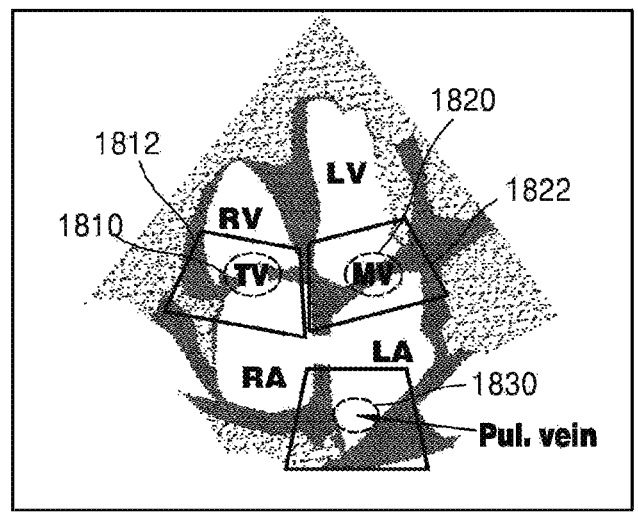
FIG. 18 illustrates an example of a method for detecting the position of a region of interest based on the boundary of a heart in an Apical 4 Chamber image according to an exemplary embodiment.

FIG. 18 illustrates an example of a method for detecting the position of a region of interest based on the boundary of a heart in an Apical 4 Chamber image according to an exemplary embodiment.

Referring to FIG. 18, the ultrasound apparatus 1000 may detect the position of the region of interest corresponding to the Apical 4 Chamber image.

In the ultrasound apparatus 1000, corresponding to the Apical 4 Chamber image, an MV sample volume, a TV sample volume, and a PV sample volume may be set as the region of interest.

The ultrasound apparatus 1000 may find the positions of the MV sample volume, the TV sample volume, and the PV sample volume based on the positions of the heart wall, the diaphragm, and the valve detected in FIG. 17.

For example, the ultrasound apparatus 1000 may detect the darkest region in the valve region located between the left heart wall and the diaphragm and determine the detected darkest region as the position of an MV sample volume 1820. Also, the ultrasound apparatus 1000 may determine the center region of the valve region located between the right heart wall and the diaphragm as the position of a TV sample volume 1810. Also, the ultrasound apparatus 1000 may detect the darkest region in the intersection region between the bottom region of the left atrium (LA) and the diaphragm and determine the detected darkest region as the position of a PV sample volume 1830.

Also, the ultrasound apparatus 1000 may display a zoom box based on the detected positions of the sample volumes. For example, the ultrasound apparatus 1000 may determine the size and position of an MV zoom box 1822 around the position of the MV sample volume based on the motion radius of the MV and the positions of the left heart wall and the diaphragm.

Also, for example, the ultrasound apparatus 1000 may determine the size and position of a TV zoom box 1812 around the position of the TV sample volume based on the motion radius of the TV and the positions of the right heart wall and the diaphragm. In this case, the ultrasound apparatus 1000 may measure the motion radiuses of the MV and the TV based on the ultrasound image at the heart contraction time and determine the sizes and positions of the MV zoom box 1822 and the TV zoom box 1812 based on the measured motion radiuses.

For example, the ultrasound apparatus 1000 may determine the size and position of the PV zoom box based on the position of the PV and the positions of the diaphragm and the left atrium (LA).

Also, the ultrasound apparatus 1000 may display the zoom boxes on the ultrasound image according to the determined sizes and positions of the zoom boxes.

Figure 19:
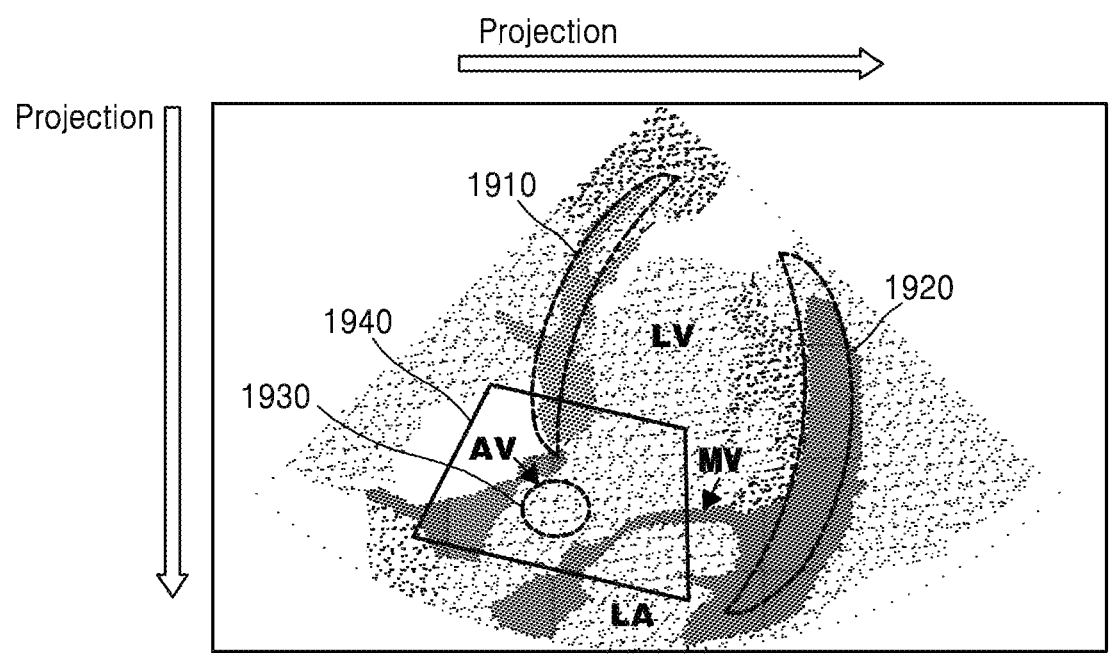
FIG. 19 illustrates an example of a method for detecting the position of a region of interest in an Apical 3 Chamber image according to an exemplary embodiment.

FIG. 19 illustrates an example of a method for detecting the position of a region of interest in an Apical 3 Chamber image according to an exemplary embodiment.

Referring to FIG. 19, the ultrasound apparatus 1000 may detect the position of the region of interest corresponding to the Apical 3 Chamber image.

In the ultrasound apparatus 1000, corresponding to the Apical 3 Chamber image, an aortic valve (AV) sample volume may be set as the region of interest.

The ultrasound apparatus 1000 may project the Apical 3 Chamber image in the vertical direction corresponding to each column and determine two regions having the highest sum of pixel values corresponding to each column as the positions of a diaphragm 1910 and a left heart wall 1920.

Also, in the Apical 3 Chamber image, a left ventricle (LV) having little motion may appear at the top end, and an image in which MV and AV moves alternately may appear at the bottom end. Accordingly, in order to detect an AV region, the ultrasound apparatus 1000 may detect the position of a region having large motion in the Apical 3 Chamber image. By detecting the position of the region having large motion in the Apical 3 Chamber image, the ultrasound apparatus 1000 may detect the position of a region including the MV and the AV except the left ventricle (LV).

Also, in the Apical 3 Chamber image, also in an image at the time of closing the AV, in which the AV appears in the ultrasound image, the AV may not appear clearer than other parts in the ultrasound image. Accordingly, the ultrasound apparatus 1000 may detect the position of the AV not by detecting the brightest region at the time of closing the AV, but by detecting the darkest region at the time of opening the AV, that is, at the time of closing the MV.

Also, the ultrasound apparatus 1000 may determine the position of an MV sample volume 1930 based on the position of the diaphragm 1910, the position of the left heart wall 1920, and the position of the darkest region detected in the image at the time of closing the MV. Also, the ultrasound apparatus 1000 may display an AV zoom box 1940 around the AV sample volume 1930.

Figure 20:
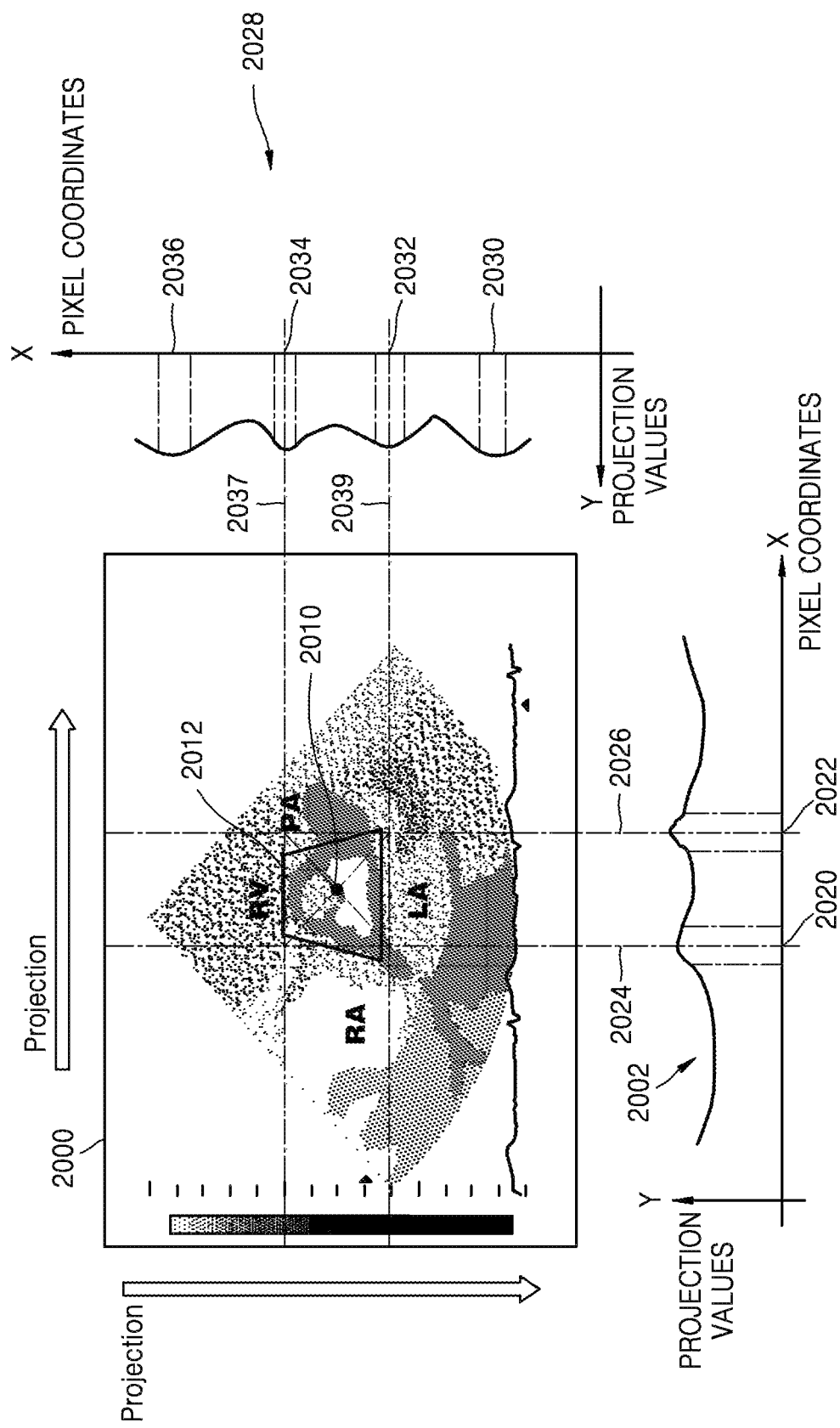
FIG. 20 illustrates an example of a method for detecting the position of a region of interest in an AV Plane image according to an exemplary embodiment.

FIG. 20 illustrates an example of a method for detecting the position of a region of interest in an AV Plane image according to an exemplary embodiment.

Referring to graph 2000, the ultrasound apparatus 1000 may detect the position of a region of interest corresponding to an AV Plane image.

In the ultrasound apparatus 1000, corresponding to the AV Plane image, an AV sample volume, a TV sample volume, a PV sample volume, and an IAS sample volume may be set as the region of interest.

After detecting the position of the AV sample volume, the ultrasound apparatus 1000 may detect the positions of the TV sample volume, the PV sample volume, and the IAS sample volume based on the detected position of the AV sample volume.

In order to detect the position of the AV sample volume, the ultrasound apparatus 1000 may project the AV Plane image horizontally or vertically. By projecting the AV Plane image horizontally or vertically, the ultrasound apparatus 1000 may calculate the brightness value of the ultrasound image corresponding to the coordinates of each row or column. Also, the ultrasound apparatus 1000 may determine a function for determining the brightness value of the ultrasound image corresponding to the coordinate value of each row or column.

Referring to graph 2002, the ultrasound apparatus 1000 may determine the horizontal boundary of the AV sample volume. For example, the ultrasound apparatus 1000 may determine the pixel positions of two regions 2020 and 2022 having the highest projection value in the vertical projection function as the horizontal boundaries 2024 and 2026 of the AV sample volume.

Referring to graph 2028, the ultrasound apparatus 1000 may determine the vertical boundary of the AV sample volume. For example, the ultrasound apparatus 1000 may determine two regions 2032 and 2034 located at the center among four regions 2030, 2032, 2034, and 2036 having the highest projection value in the horizontal projection function as the vertical boundaries 2037 and 2039 of the AV sample volume.

By determining the vertical and horizontal boundaries of the AV sample volume, the ultrasound apparatus 1000 may determine a tetragon surrounding the AV sample volume based on the determined boundaries. The ultrasound apparatus 1000 may determine the position of the AV sample volume based on a center point 2010 of the determined tetragon. For example, within the tetragon, the ultrasound apparatus 1000 may rotate 360 degrees around the center point 2010, detect the pixels having a brightness value greater than or equal to a reference value according to the distance from the center point, and determine a region including the detected pixels as a region of the AV sample volume. Also, the ultrasound apparatus 1000 may determine the position of an AV zoom box 2012 around the determined AV sample volume region.

Figure 21:
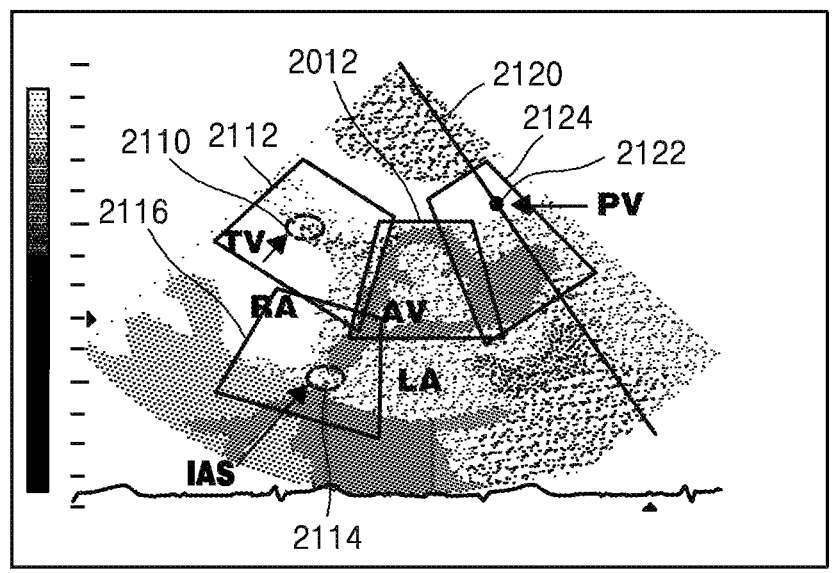
FIG. 21 illustrates another example of a method for detecting the position of a region of interest in an AV Plane image according to an exemplary embodiment.

FIG. 21 illustrates another example of a method for detecting the position of a region of interest in an AV Plane image according to an exemplary embodiment.

Also, in order to detect the position of a TV sample volume 2110, the ultrasound apparatus 1000 may horizontally project a region located at a predetermined distance from the left of the AV zoom box 2012, and detect the pixel coordinates of the brightest region in the projected row as the vertical coordinates of the TV sample volume. Also, the ultrasound apparatus 1000 may vertically project the same region and detect the pixel coordinates of the darkest region in the projected column as the horizontal coordinates of the TV sample volume. Also, the ultrasound apparatus 1000 may determine the position of a TV zoom box 2112 around the detected position of the TV sample volume 2110.

Also, in order to detect the position of an M line 2120, the ultrasound apparatus 1000 may divide a region, which is located at a predetermined distance from the right of the AV zoom box, into constant sections along the horizontal direction. Then, the ultrasound apparatus 1000 may perform vertical projection in the respective constant sections. Then, the ultrasound apparatus 1000 may determine the darkest section among the vertically-projected sections as the position of the M line 2120.

Also, in order to detect the position of a PV sample volume 2122, the ultrasound apparatus 1000 may horizontally project a region located at a predetermined upward distance from the top boundary of the AV zoom box, and detect the vertical coordinates of the brightest region and the darkest region. Then, the ultrasound apparatus 1000 may calculate the halfway point between the detected brightest and darkest regions and determine the calculated halfway point as the position of the PV sample volume 2122. Also, the ultrasound apparatus 1000 may determine a region located at a predetermined distance from the position of the PV sample volume 2122 as a PV zoom box 2124.

Also, in order to detect the position of an IAS sample volume 2114, the ultrasound apparatus 1000 may horizontally and vertically project a region located at a predetermined downward distance from the bottom boundary of the AV zoom box, and detect the coordinates of the brightest region as the position of the IAS sample volume 2114. Also, the ultrasound apparatus 1000 may determine a region located at a predetermined distance from the position of the IAS sample volume 2114 as an IAS zoom box 2116.

Figure 22:
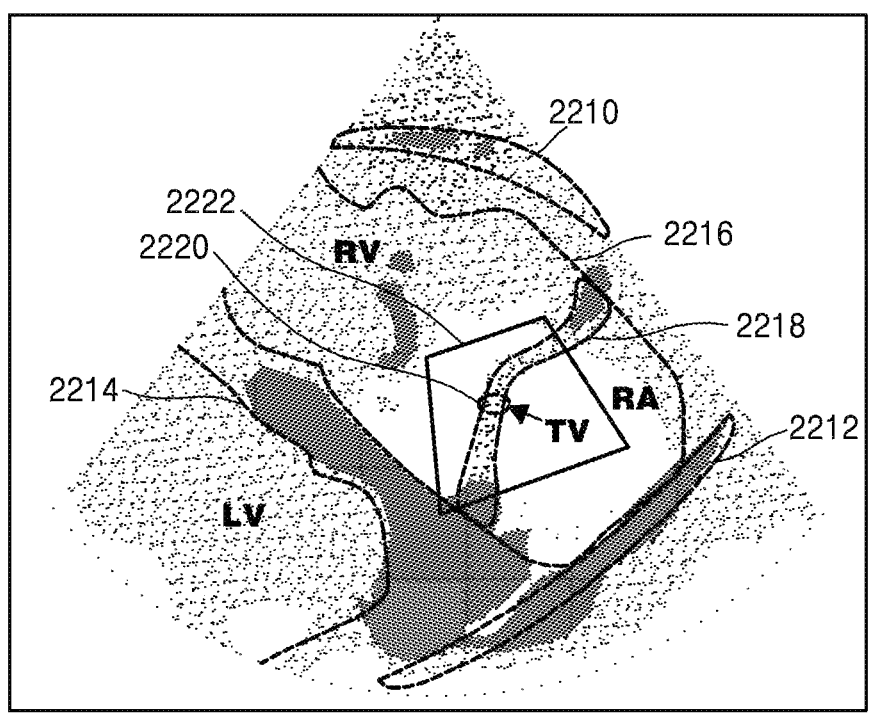
FIG. 22 illustrates an example of a method for detecting the position of a region of interest in an RV Inflow Plane image according to an exemplary embodiment.

FIG. 22 illustrates an example of a method for detecting the position of a region of interest in an RV Inflow Plane image according to an exemplary embodiment.

Referring to FIG. 22, the ultrasound apparatus 1000 may detect the position of a region of interest corresponding to an RV Inflow Plane image.

In the ultrasound apparatus 1000, corresponding to the RV Inflow Plane image, a TV sample volume may be set as the region of interest.

In order to detect the position of a TV sample volume 2220, the ultrasound apparatus 1000 may project the RV Inflow Plane image horizontally or vertically. By projecting the RV Inflow Plane image horizontally, the ultrasound apparatus 1000 may detect the boundaries 2210 and 2212 of the heart. Also, in order to discriminate between the left and right of the heart, based on a region expansion method, the ultrasound apparatus 1000 may determine the position of a right region 2216 of the heart including a right ventricle (RV) and a right atrium (RA) and the position of a left region 2214 of the heart including a left ventricle (LV). Also, the ultrasound apparatus 1000 may detect a boundary 2218 between the right ventricle (RV) and the right atrium (RA) in the right region 2216 of the heart determined by the region expansion method. Also, the ultrasound apparatus 1000 may determine the center point of the detected boundary 2218 as the position of the TV sample volume 2220. Accordingly, the ultrasound apparatus 1000 may display a TV zoom box 2222 based on the determined position of the TV sample volume 2220.

Figure 23:
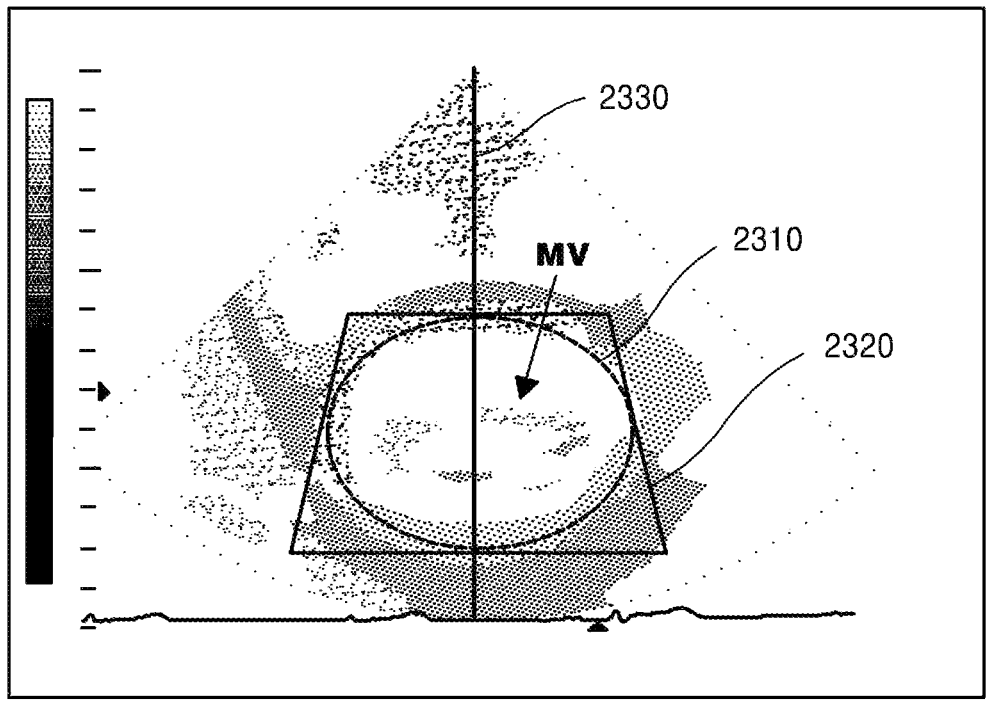
FIG. 23 illustrates an example of a method for detecting the position of a region of interest corresponding to a Basal Plane image by an ultrasound apparatus according to an exemplary embodiment.

FIG. 23 illustrates an example of a method for detecting the position of a region of interest corresponding to a Basal Plane image by the ultrasound apparatus 1000 according to an exemplary embodiment.

In the ultrasound apparatus 1000, corresponding to the Basal Plane image, an MV sample volume and a Basal Guide line may be set as the region of interest.

The Basal image may be an image in which a heart wall appears in an elliptical shape. Accordingly, the ultrasound apparatus 1000 may determine the position of an inner boundary 2310 of the heart by an ellipse fitting method. Also, the ultrasound apparatus 1000 may determine the inner boundary 2310 of the heart in the Basal image by a circle fitting method. The ultrasound apparatus 1000 may determine a tetragon contacting the fitted ellipse or circle as an MV zoom box 2320.

Also, the ultrasound apparatus 1000 may determine a line segment passing from an apex of the basal image through the center of the fitted ellipse or circle as a basal guide line 2330.

Since the position of the heart wall changes continuously according to the heartbeat and breath of the object, the ultrasound apparatus 1000 may tracking the heart wall in order to accurately measuring the basal guide line 2330. For example, the ultrasound apparatus 1000 may perform horizontal projection and vertical projection for each frame of the Basal image. By performing the horizontal projection and the vertical projection, the ultrasound apparatus 1000 may detect the size and position of the heart wall for each frame. Then, the ultrasound apparatus 1000 may calculate the accurate position of the basal guide line 2330 by averaging the positions of the tracked heart wall.

Figure 24:
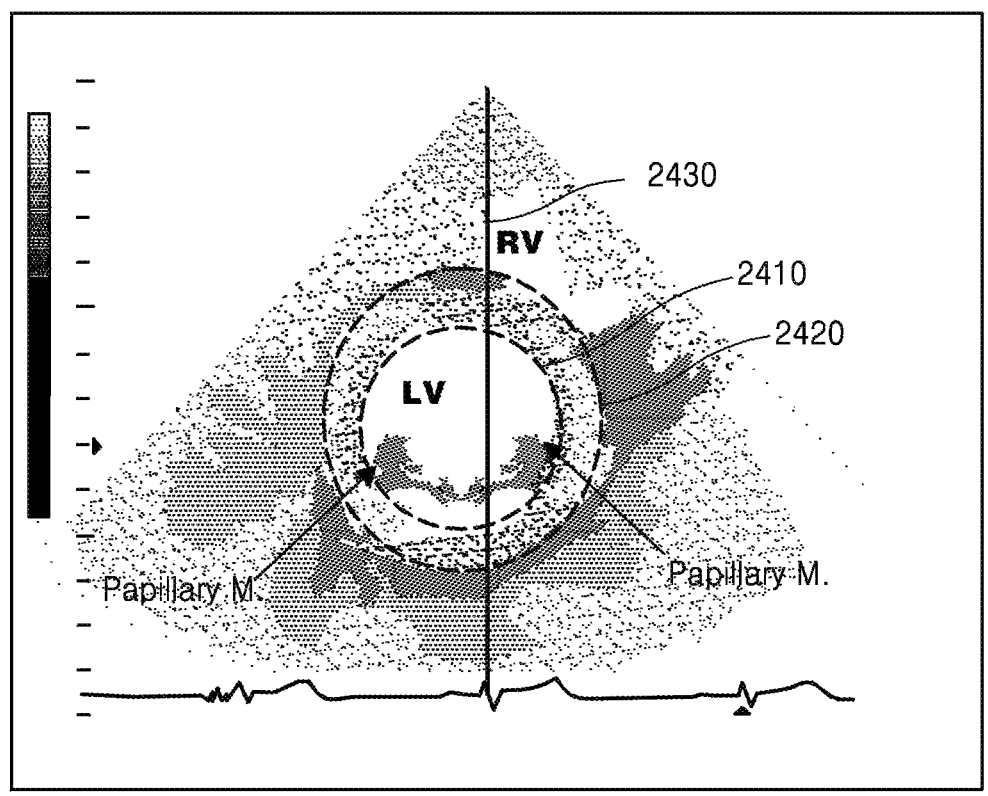
FIG. 24 illustrates an example of a method for detecting the position of a region of interest corresponding to a Mid Plane image by an ultrasound apparatus according to an exemplary embodiment.

FIG. 24 illustrates an example of a method for detecting the position of a region of interest corresponding to a Mid Plane image by the ultrasound apparatus 1000 according to an exemplary embodiment.

In the ultrasound apparatus 1000, corresponding to the Mid Plane image, a papillary muscle region and a midguide line may be set as the region of interest.

As illustrated in FIG. 24, the Mid Plane image may be an image in which a heart wall appears under a left ventricle (LV) and a right ventricle (RV) appears over the left ventricle (LV) with a diaphragm therebetween. Accordingly, in the Mid Plane image, the left ventricle (LV) may be surrounded by double ellipses 2410 and 2420.

The ultrasound apparatus 1000 may detect the position of the double ellipses 2410 and 2420 by using a double ellipse model. Also, the ultrasound apparatus 1000 may detect the position of the inner ellipse 2410 as the position of the left ventricle (LV) based on the detected position of the double ellipses 2410 and 2420.

Also, in order to detect the papillary muscle region, the ultrasound apparatus 1000 may detect the position of the papillary muscle region in the inner ellipse region by using an adaptive thresholding method.

By detecting the position of the papillary muscle region, the ultrasound apparatus 1000 may determine the halfway point between the left and right papillary muscle regions as a center point of the left ventricle (LV). Accordingly, the ultrasound apparatus 1000 may determine a line segment connecting an apex and a halfway point of the left ventricle (LV) as a midguide line 2430.

Figure 25:
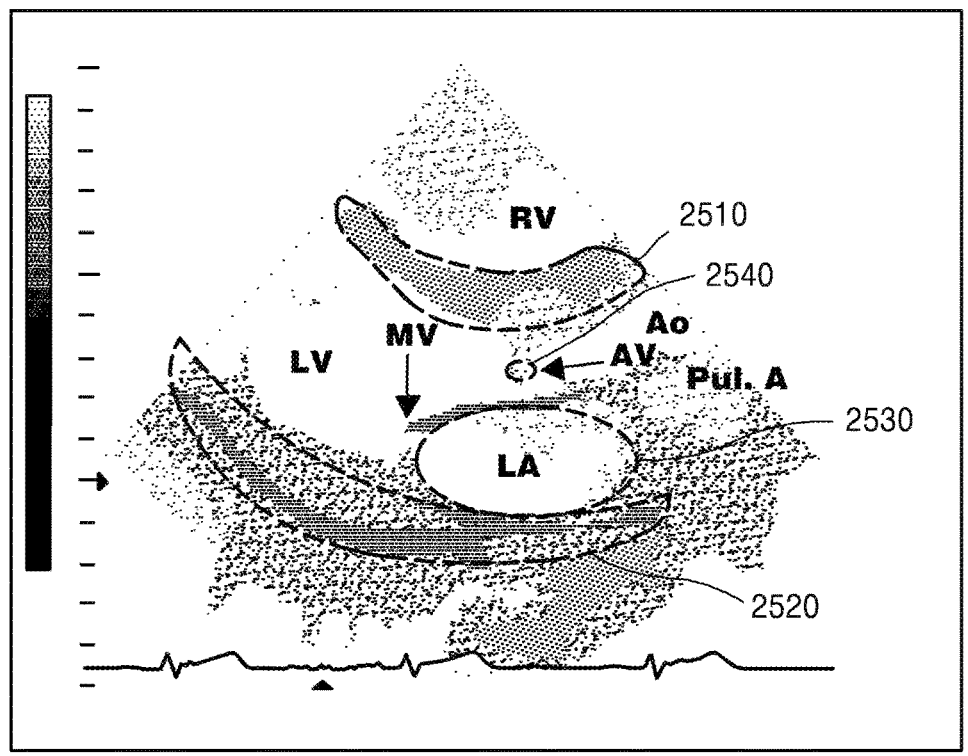
FIG. 25 illustrates an example of a method for detecting the position of a region of interest corresponding to a PLAX image by an ultrasound apparatus according to an exemplary embodiment.

FIG. 25 illustrates an example of a method for detecting the position of a region of interest corresponding to a PLAX image by the ultrasound apparatus 1000 according to an exemplary embodiment.

In the ultrasound apparatus 1000, corresponding to the PLAX image, an AV sample volume may be set as the region of interest.

The ultrasound apparatus 1000 may project the PLAX image horizontally corresponding to each row and determine two regions having the highest sum of pixel values corresponding to each row as the positions of a diaphragm 2510 and a heart wall 2520 at the bottom of the left ventricle (LV).

Also, the ultrasound apparatus 1000 may detect the position of a left atrium (LA) by the ellipse fitting method. Also, the ultrasound apparatus 1000 may detect the positions of an MV sample volume region and an MV tip based on the major-axis direction of an ellipse 2530 detected by the ellipse fitting method and the angle of the heart wall 2520 at the bottom of the left ventricle (LV).

Also, the ultrasound apparatus 1000 may detect a region of an AV sample volume 2540 based on a line segment connecting an apex and the center of the left atrium (LA).

Figure 26:
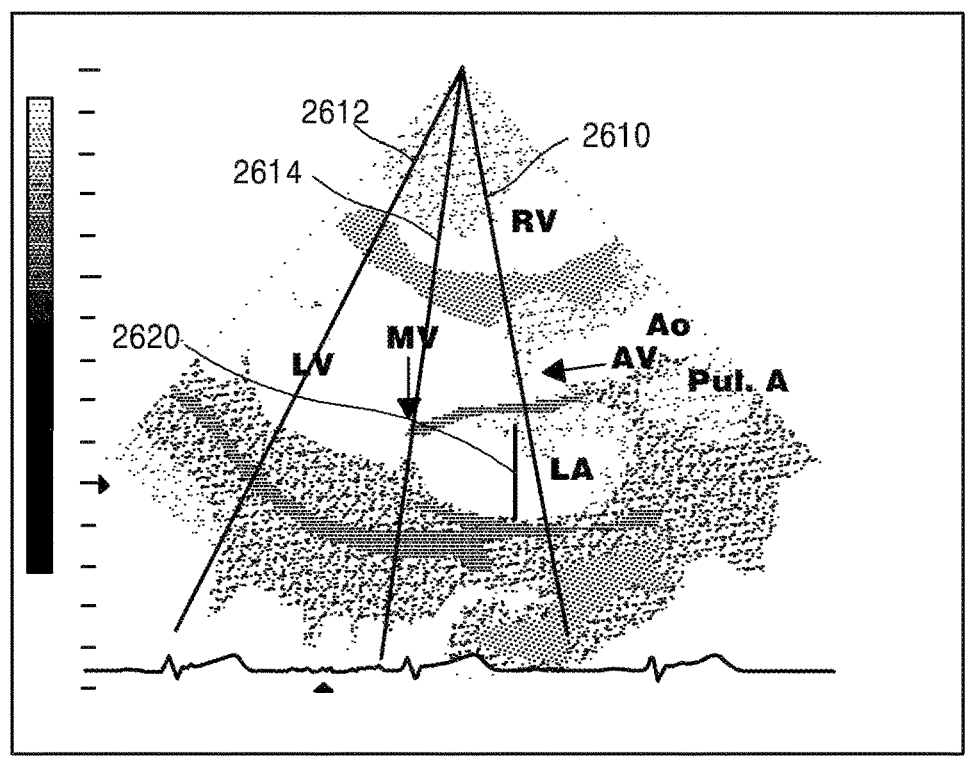
FIG. 26 illustrates another example of a method for detecting the position of a region of interest corresponding to a PLAX image by an ultrasound apparatus according to an exemplary embodiment.

FIG. 26 illustrates another example of a method for detecting the position of a region of interest corresponding to a PLAX image by the ultrasound apparatus 1000 according to an exemplary embodiment.

In the ultrasound apparatus 1000, corresponding to the PLAX image, an MV sample volume and a left atrium (LA) AP diameter may be set as the region of interest.

The ultrasound apparatus 1000 may determine a line segment 2614 connecting the apex of the PLAX image and the MV tip, a line segment 2610 connecting the apex and the center of the left atrium (LA), and a line segment 2612 connecting regions located at a largest distance from the apex in the boundary of the heart wall at the bottom of the left ventricle (LV), as M-lines.

Also, the ultrasound apparatus 1000 may detect a heart contraction last time point by tracking a left atrium (LA) and an aorta wall. Then, the ultrasound apparatus 1000 may determine the minor-axis length of a fitted ellipse as the length of a left atrium (LA) AP diameter 2620 at the heart contraction last time point.

Figure 27:
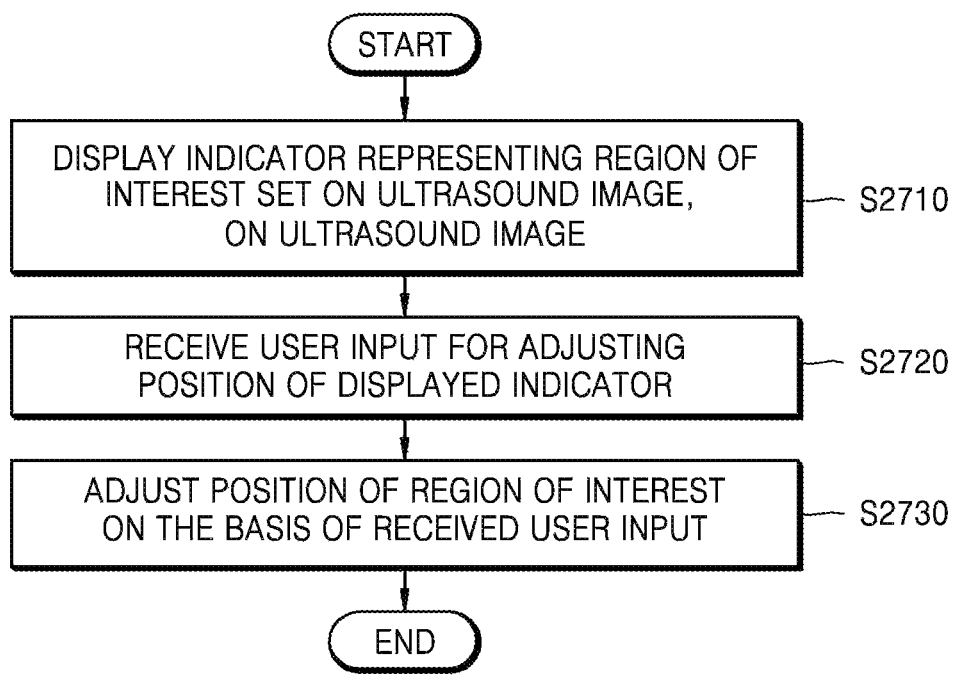
FIG. 27 is a flowchart of a method for adjusting a region of interest based on a user input by an ultrasound apparatus according to an exemplary embodiment.

FIG. 27 is a flowchart of a method for adjusting a region of interest based on a user input by the ultrasound apparatus 1000 according to an exemplary embodiment.

Referring to FIG. 27, in operation S2710, the ultrasound apparatus 1000 may display an indicator, which represents at least one region of interest set on the ultrasound image, on the ultrasound image.

The ultrasound apparatus 1000 may determine a view plane of the ultrasound image and display an indicator representing at least one of a plurality of regions of interest corresponding to the determined view plane. For example, in the ultrasound apparatus 1000, corresponding to the Apical 4 Chamber image, an MV sample volume, a TV sample volume, and a PV sample volume may be set as the region of interest. Also, in the ultrasound apparatus 1000, corresponding to the Apical 4 Chamber image, an MV sample volume may be set to be automatically displayed. Also, in the ultrasound apparatus 1000, a zoom box may be set as an indicator representing the MV sample volume.

Accordingly, when the determined view plane of the ultrasound image is the Apical 4 Chamber image, the ultrasound apparatus 1000 may determine the positions of the MV sample volume, the TV sample volume, and the PV sample volume in the ultrasound image. Then, the ultrasound apparatus 1000 may display an MV zoom box representing the MV sample volume at the position of the MV sample volume.

In operation 52720, the ultrasound apparatus 1000 may receive a user input for adjusting the position of the displayed indicator.

The ultrasound apparatus 1000 may display a user interface for adjusting the position of the displayed indicator. The user interface may be provided in the form of a menu.

Also, the user interface may be an interface that may be directly touched and moved by the user. Also, the user interface may be an interface in which a displayed indicator moves when the user moves a track ball attached to a control panel.

The ultrasound apparatus 1000 may receive a user input for moving the indicator through the user interface.

In operation 52730, the ultrasound apparatus 1000 may adjust the position of a plurality of regions of interest based on the received user input.

When receiving the user input for moving the displayed indicator, the ultrasound apparatus 1000 may change the position of the region of interest represented by the indicator into the position moved by the user input.

When the position of the region of interest is changed, the ultrasound apparatus 1000 may adjust the position of the region of interest represented by the indicator and the position of a plurality of regions of interest corresponding to the view plane.

For example, in the case of an AOR image, a TV sample volume region, a PV sample volume region, and an IAS sample volume region may be determined based on an AV sample volume region. When the ultrasound image is determined on an AOR view plane image, the ultrasound apparatus 1000 may first determine the position of the AV sample volume region. In this case, the ultrasound apparatus 1000 may determine the position of the AV sample volume region as another position on the ultrasound image, not the AV region. When the position of the AV sample volume region is inaccurate, the positions of the TV sample volume region, the PV sample volume region, and the IAS sample volume region may also be inaccurate.

In this case, the ultrasound apparatus 1000 may receive a user input for adjusting the position of the AV sample volume. The ultrasound apparatus 1000 may determine again the positions of the TV sample volume region, the PV sample volume region, and the IAS sample volume region based on the adjusted position of the AV sample volume.

Thus, when the user changes the region of interest as the PV sample volume, the ultrasound apparatus 1000 may display a PV zoom box at the accurate position of the PV sample volume.

FIGS. 28A, 28B, 28C, and 28D illustrate an example of a method for adjusting a region of interest based on a user input by the ultrasound apparatus 1000 according to an exemplary embodiment.

Figure 28A:
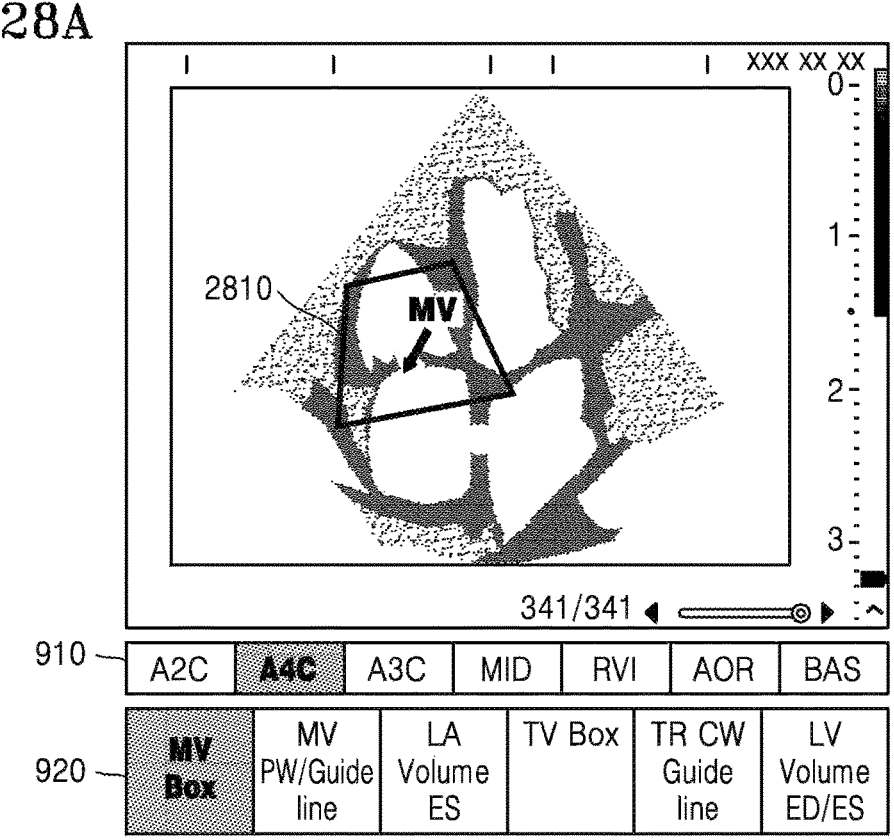
FIGS. 28A, 28B, 28C, and 28D illustrate an example of a method for adjusting a region of interest based on a user input by an ultrasound apparatus according to an exemplary embodiment.

Referring to FIG. 28A, the ultrasound apparatus 1000 may capture an image of a heart of the object on an Apical 4 Chamber plane and display the captured ultrasound image on the screen.

Also, the ultrasound apparatus 1000 may acquire information about a region of interest predetermined corresponding to the Apical 4 Chamber image. In the ultrasound apparatus 1000, corresponding to the Apical 4 Chamber image, an MV sample volume, a TV sample volume, and a PV sample volume may be set as the region of interest. Accordingly, the ultrasound apparatus 1000 may detect the positions of the MV sample volume, the TV sample volume, and the PV sample volume in the ultrasound image.

Also, in the ultrasound apparatus 1000, an MV sample volume among a plurality of regions of interest corresponding to Apical 4 Chamber may be set to be automatically displayed.

The ultrasound apparatus 1000 may determine the position of the MV sample volume region as another position on the ultrasound image, not the MV region. For example, when the actual coordinates of the position of a diaphragm are determined as the coordinates of the position of a left heart wall, the ultrasound apparatus 1000 may determine the position of the MV sample volume as the actual position of the TV, not the region in which the MV is actually located. Accordingly, the ultrasound apparatus 1000 may display an MV zoom box 2810 at the actual position of the TV sample volume. Also, since the position of the AV sample volume is determined to be different from the actual position, the ultrasound apparatus 1000 may determine the positions of the TV sample volume and the PV sample volume to be different from the actual positions thereof.

Figure 28B:
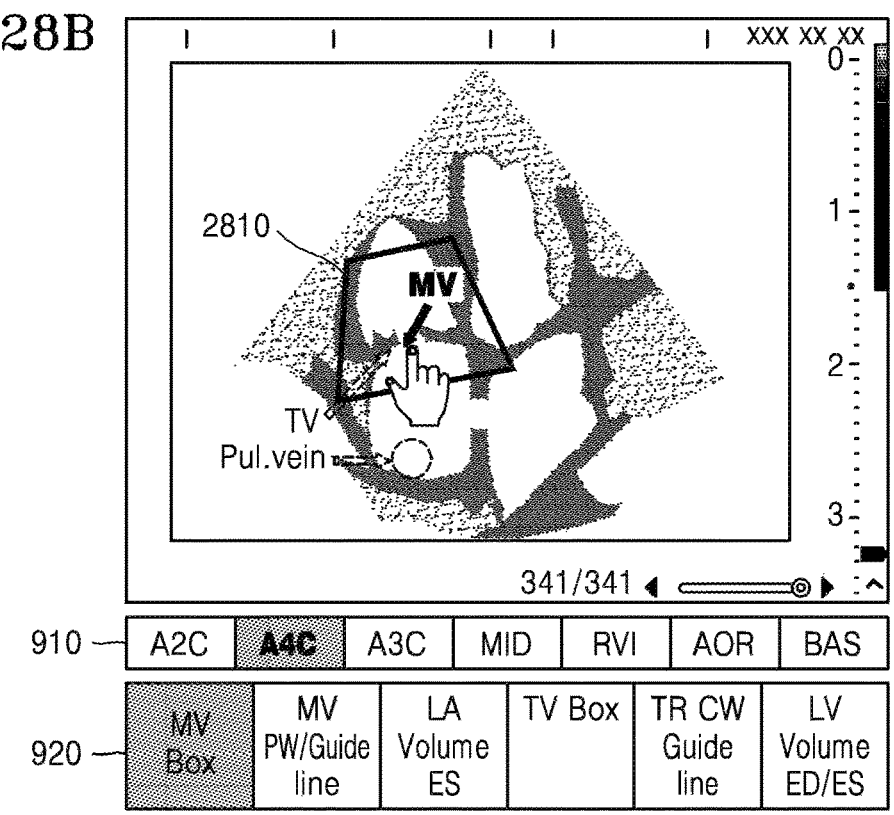

Referring to FIG. 28B, the ultrasound apparatus 1000 may receive a user input for adjusting the position of the displayed indicator.

For example, when the user touches the MV zoom box 2810, the ultrasound apparatus 1000 may enable a user interface for moving the position of the MV zoom box 2810. For example, the ultrasound apparatus 1000 may display information indicating that the position of the MV zoom box 2810 may be moved by the user input.

Also, by enabling the user interface for moving the position of the MV zoom box 2810, the ultrasound apparatus 1000 may display the position of the MV sample volume and the positions of the other regions of interest corresponding to Apical 4 Chamber. For example, the ultrasound apparatus 1000 may also display information representing the positions of the TV sample volume and the PV sample volume determined by the ultrasound apparatus 1000.

Figure 28C:
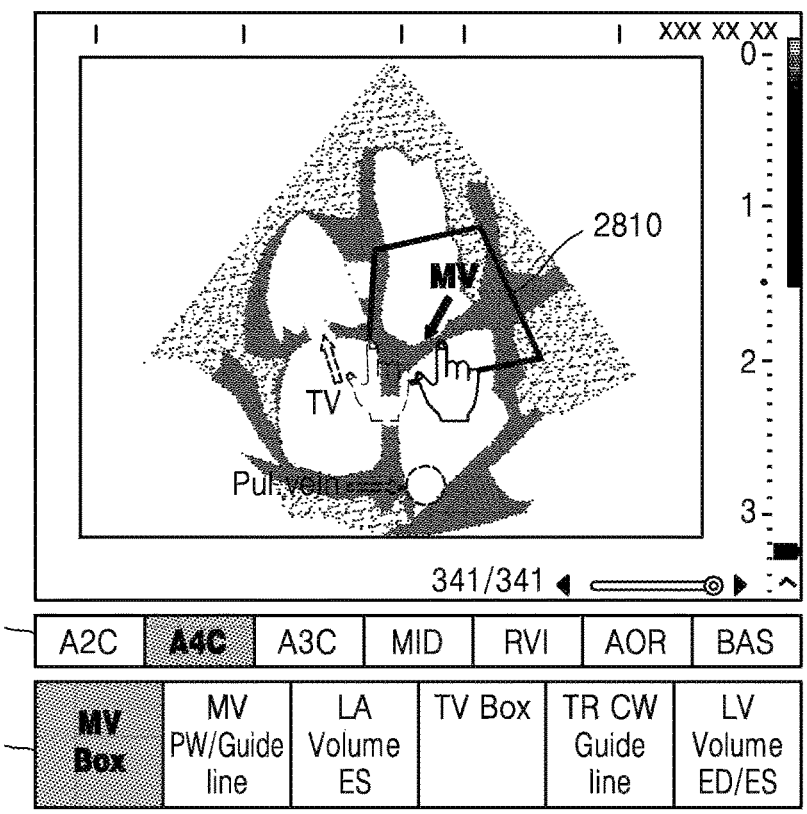

Referring to FIG. 28C, the ultrasound apparatus 1000 may change the position of the region of interest based on the user input.

Also, the ultrasound apparatus 1000 may change the position of the MV sample volume according to the user input for moving the position of the MV zoom box 2810. Also, based on the changed position of the MV sample volume, the ultrasound apparatus 1000 may change the positions of the other regions of interest corresponding to Apical 4 Chamber. For example, the ultrasound apparatus 1000 may recalculate the positions of the left heart wall and the diaphragm based on the user input for moving the MV zoom box 2810 to the right. Accordingly, the ultrasound apparatus 1000 may detect the accurate positions of the left heart wall and the diaphragm.

By recalculating the positions of the left heart wall and the diaphragm, the ultrasound apparatus 1000 may detect the accurate positions of the TV sample volume and the PV sample volume. Also, the ultrasound apparatus 1000 may display information representing the recalculated positions of the TV sample volume and the PV sample volume.

Figure 28D:
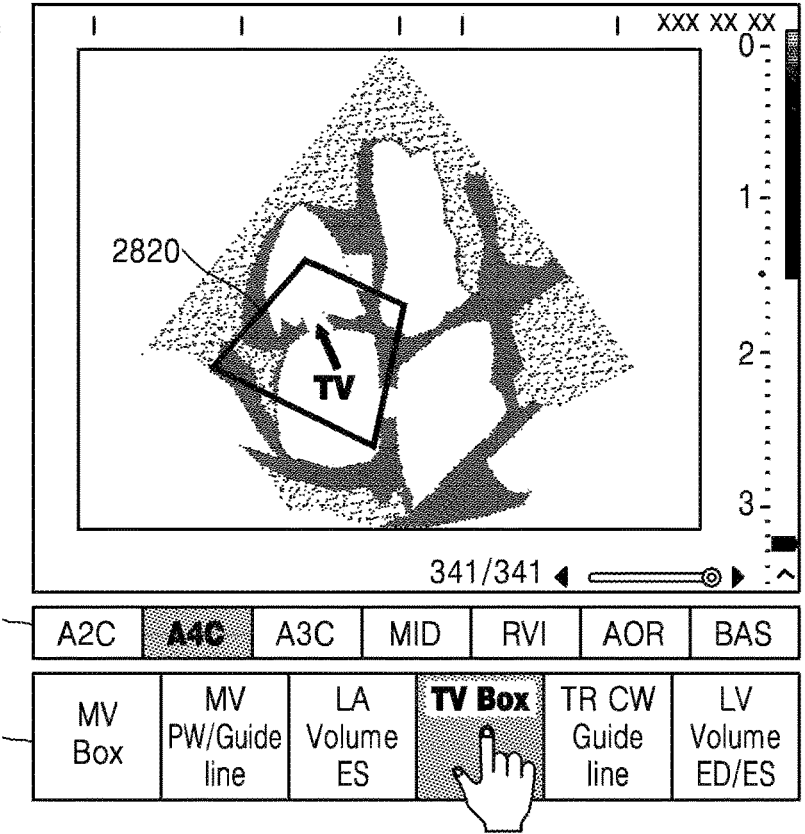

Referring to FIG. 28D, the ultrasound apparatus 1000 may receive a user input for changing the region of interest. When receiving a user input for changing the region of interest into the TV sample volume, the ultrasound apparatus 1000 may display a TV zoom box 2820 at the recalculated accurate position of the TV sample volume.

FIG. 29 is a block diagram of the ultrasound apparatus 1000 according to an exemplary embodiment.

The ultrasound apparatus 1000 according to an exemplary embodiment may include a display or displays 1100, an image determiner 1200, and a controller 1300. However, all of the illustrated components are not necessary components. The ultrasound apparatus 1000 may include more or less components than the illustrated components.

The display 1100 may include a touchscreen by forming a layer structure with a touch pad. That is, the display 1100 according to an exemplary embodiment may be used as an input unit and an output unit.

Also, the display 1100 may display an ultrasound image on the screen of the ultrasound apparatus 1000. Also, the display 1100 may display a user interface for measuring an ultrasound image on the screen of the ultrasound apparatus 1000.

Also, the display 1100 may display a user interface for changing a view plane determined for an ultrasound image into one of a plurality of view planes on the screen. The user interface for changing into one of the plurality of view planes may include identification information of the plurality of view planes. Also, the identification information of the plurality of view planes may be arranged based on an order preset corresponding to the determined view plane.

Also, the display 1100 may display an indicator representing at least one of a plurality of regions of interest on the ultrasound image based on the position of the plurality of regions of interest.

Also, the display 1100 may display a user interface for changing the region of interest set on the ultrasound image into one of the plurality of regions of interest corresponding to the determined view plane.

Also, the display 1100 may display an indicator representing at least one of the plurality of regions of interest corresponding to the view plane.

The image determiner 1200 may determine a view plane, on which the ultrasound image is captured, among a plurality of view planes.

Also, the image determiner 1200 may include a plurality of classifiers that classify the ultrasound image as one of a predetermined number of view plane images. In this case, the predetermined number of view plane images may be selected as different combinations among a plurality of view plane images corresponding to the plurality of view planes. Also, the predetermined number of view plane images may be two view plane images.

In general, the controller 1300 may control operations of the ultrasound apparatus 1000. That is, the controller 1300 may control the display 1100 and the image determiner 1200.

Also, the controller 1300 may determine a view plane, on which the ultrasound image is captured, among a plurality of view planes based on the result value of the image determiner 1200.

Also, the controller 1300 may set at least one of the plurality of regions of interest corresponding to the determined view plane on the ultrasound image.

Also, the controller 1300 may receive a user input for selecting one of the plurality of view planes and set at least one of a plurality of regions of interest corresponding to the selected view plane on the ultrasound image.

Also, the controller 1300 may acquire information about a plurality of regions of interest corresponding to the view plane and determine a position of the plurality of regions of interest in the ultrasound image based on the information about the plurality of regions of interest.

Also, the controller 1300 may receive a user input for selecting one of the plurality of regions of interest corresponding to the determined view plane and set the selected region of interest on the ultrasound image based on the position of the plurality of regions of interest.

Also, the controller 1300 may calculate the sum of pixel values in a row or a column of the ultrasound image. The controller 1300 may calculate the brightness value of the ultrasound image corresponding to the coordinates of each row or column by calculating the sum of pixel values in each row or column of the ultrasound image. Also, the controller 1300 may generate a function for determining the brightness value of the ultrasound image corresponding to the coordinate value of each row or column.

Also, the controller 1300 may determine the position of the plurality of regions of interest in the ultrasound image based on the sum of the pixel values in the row or the column of the ultrasound image.

Also, the controller 1300 may adjust the position of the plurality of regions of interest based on the received user input.

FIG. 30 is a block diagram of the ultrasound apparatus 1000 according to another exemplary embodiment.

The ultrasound apparatus 1000 according to another exemplary embodiment may include a probe or probes 20, an ultrasound transceiver 100, an image processor 200, a communicator 300, and a memory 400 in addition to the display 1100, the image determiner 1200, and the controller 1300, where these components may be connected to one another via buses 700.

The ultrasound apparatus 1000 may be embodied as a cart type ultrasound apparatus and a portable ultrasound apparatus. Examples of the portable ultrasound apparatus 1000 may include a picture archiving and communication system (PACS) viewer, a smart phone, a laptop computer, a personal digital assistant (PDA), and a tablet personal computer (PC). However, exemplary embodiments are not limited thereto.

The probe 20 transmits an ultrasound signal to an object 10 according to a driving signal applied from the ultrasound transceiver 100 and receives an echo signal reflected from the object 10. The probe 20 includes a plurality of transducers, and the plurality of transducers oscillate according to an electrical signal transmitted thereto and generate an ultrasonic wave, that is, acoustic energy. Also, the probe 20 may be connected to a main body of the ultrasound apparatus 1000 by wire or wirelessly.

A transmitter 110 supplies a driving signal to the probe 20 and includes a pulse generator 112, a transmission delayer 114, and a pulser 116. The pulse generator 112 generates pulses for forming transmission ultrasonic waves according to a predetermined pulse repetition frequency (PRF), and the transmission delayer 114 applies a delay time for determining transmission directionality to the pulses. The pulses to which a delay time is applied correspond to a plurality of piezoelectric vibrators included in the probe 20, respectively. The pulser 116 applies a driving signal (or a driving pulse) to the probe 20 at a timing corresponding to each pulse to which a delay time is applied.

A receiver 120 generates ultrasound data by processing echo signals received from the probe 20 and may include an amplifier 122, an analog-to-digital converter (ADC) 124, a reception delayer 126, and a adder 128. The amplifier 122 amplifies echo signals in each channel, and the ADC 124 converts the amplified analog echo signals into digital signals. The reception delayer 126 applies delay times for determining reception directionality to the digital-converted echo signals, and the adder 128 generates ultrasound data by summing the echo signals processed by the reception delayer 166 and outputs the echo signals to a data processor 210 of the image processor 200.

The image processor 200 generates an ultrasound image by scan-converting ultrasound data generated by the ultrasound transceiver 100 and displays the ultrasound image. The ultrasound image may be a gray-scale ultrasound image obtained by scanning the object according to an amplitude (A) mode, a brightness (B) mode, and a motion (M) mode, and a Doppler image of a motion of the object. The Doppler image may include a bloodstream Doppler image (also referred to as a color Doppler image) representing a flow of blood, a tissue Doppler image representing a motion of a tissue, and a spectral Doppler image representing a movement speed of the object in a waveform.

A B mode processor 212 extracts B mode components from ultrasound data and processes the B mode components. An image generator 220 may generate an ultrasound image representing signal intensities as brightness based on the B mode components extracted by the B mode processor 212.

Likewise, a Doppler processor 214 may extract Doppler components from ultrasound data, and the image generator 220 may generate a Doppler image representing a motion of the object 1 as colors or waveforms based on the extracted Doppler components.

The image generator 220 according to an exemplary embodiment may generate a three-dimensional (3D) ultrasound image through volume-rendering of volume data and may also generate an elasticity image that visualizes the deformation of the object 10 due to a pressure. The image generator 220 may display various additional information on the ultrasound image by using texts and graphics. The generated ultrasound image may be stored in the memory 400.

The communicator 300 is connected by wire or wirelessly to a network 30 to communicate with an external device or a server. The communicator 300 may exchange data with a hospital server or other medical apparatuses in a hospital connected through a picture archiving and communication system (PACS). Also, the communicator 300 may perform data communication according to the Digital Imaging and Communications in Medicine (DICOM) standard.

The communicator 300 may transmit and receive data related to diagnosis of an object, such as an ultrasound image, ultrasound data, and Doppler data of the object, through the network 30 and may also transmit and receive medical images captured by other medical devices, such as a CT image, an MR image, and an X-ray image. The communicator 300 may receive information related to the diagnosis history or treatment schedule of a patient from a server and may utilize the information to diagnose the object. The communicator 300 may perform data communication with a server or a medical apparatus in a hospital, and/or with a portable terminal of a doctor or a patient.

The communicator 300 may be connected by wire or wirelessly to the network 30 to exchange data with a server 32, a medical apparatus 34, or a portable terminal 36. The communicator 300 may include one or more components that enable communication with external devices, and may include, for example, a short-range communicator 310, a wired communicator 320, and a mobile communicator 330.

The short-range communicator 310 refers to a module for short-range communication within a predetermined distance. Examples of short-range communication techniques according to an exemplary embodiment may include wireless LAN, Wi-Fi, Bluetooth, Zigbee, Wi-Fi Direct (WFD), ultra wideband (UWB), infrared data association (IrDA), Bluetooth Low Energy (BLE), and near field communication (NFC); however, exemplary embodiments are not limited thereto.

The wired communicator 320 refers to a module for communication using electrical signals or optical signals. Examples of wired communication techniques according to an exemplary embodiment may include a pair cable, a coaxial cable, an optical fiber cable, and an Ethernet cable.

The mobile communicator 330 transmits and receives wireless signals to and from at least one of a base station, an external terminal, and a server on a mobile communication network. Herein, the wireless signals may include voice call signals, video call signals, or various types of data for transmission and reception of text/multimedia messages.

The memory 400 stores various data processed by the ultrasound apparatus 1000. For example, the memory 400 may store medical data related to diagnosis of an object, such as ultrasound data and ultrasound images that are input or output and may also store algorithms or programs to be executed in the ultrasound apparatus 1000. For example, corresponding to measurement tools, the ultrasound apparatus 1000 may store interesting information to be measured, a method for determining a region of interest, and a method for measuring interesting information about a region of interest.

The memory 400 may be embodied as at least one of various storage media such as a flash memory, a hard disk drive, and an electrically erasable programmable read-only memory (EEPROM). Also, the ultrasound apparatus 1000 may utilize a web storage or a cloud server that functions as the memory 400 online.

The input device 500 may include a unit through which the user inputs data for controlling the ultrasound apparatus 1000. The input device 500 may further include various input units such as an electrocardiogram measuring module, a breath measuring module, a voice recognition sensor, a gesture recognition sensor, a fingerprint recognition sensor, an iris recognition sensor, a depth sensor, and a distance sensor. Also, the input device 500 may include, but is not limited to, a control panel, a key pad, a dome switch, a touch pad (e.g., a capacitive overlay type, a resistive overlay type, an infrared beam type, a surface acoustic wave type, an integral strain gauge type, or a piezoelectric type), a touch screen, a jog wheel, and a jog switch. Also, the input device 500 may receive a user input for changing the view plane. Also, the input device 500 may receive a user input for changing the region of interest. Also, the input device 500 may receive a user input for adjusting the position of a displayed indicator.

All or some of the probe 20, the ultrasound transceiver 100, the image processor 200, the communicator 300, the memory 400, the input device 500, and the controller 1300 may be operated by software modules. However, exemplary embodiments are not limited thereto, and some of the above components may be operated by hardware modules. Also, at least one of the ultrasound transceiver 100, the image processor 200, and the communicator 300 may be included in the controller 1300; however, exemplary embodiments are not limited thereto.

The methods according to the exemplary embodiments may be embodied in the form of program commands executable through various computer means, which may be recorded on a computer-readable recording medium. The computer-readable recording medium may include program commands, data files, and data structures either alone or in combination. The program commands recorded on the computer-readable recording medium may be those that are especially designed and configured for the inventive concept, or may be those that are known and available to computer programmers skilled in the art. Examples of the computer-readable recording medium include magnetic recording media such as hard disks, floppy disks, and magnetic tapes, optical recording media such as CD-ROMs and DVDs, magneto-optical recording media such as floptical disks, and hardware devices such as ROMs, RAMs, and flash memories that are especially configured to store and execute program commands. Examples of the program commands include machine language codes that may be generated by a compiler, and high-level language codes that may be executed by a computer by using an interpreter.

The foregoing exemplary embodiments and advantages are merely exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasound medical imaging method in an ultrasound apparatus including a controller, the ultrasound medical imaging method comprising:
    displaying an ultrasound image on a screen;
    determining, by the controller, an image view plane of the ultrasound image as a first view plane among a plurality of view planes, by performing, in steps, a series of classifiers that classify the ultrasound image as one view plane image from a predetermined number of view plane images at each of the steps;
    acquiring, by the controller, information about a plurality of regions of interest corresponding to the first view plane;
    determining, by the controller, positions of the plurality of regions of interest in the ultrasound image, based on the acquired information of the plurality of regions of interest;
    displaying a first indicator representing a first region of interest among the plurality of regions of interest and a second indicator representing a second region of interest among the plurality of regions of interest, on the ultrasound image based on the positions, wherein a form of the first indicator is determined, by the controller, according to the first region of interest and the first view plane, and a form of the second indicator is determined, by the controller, according to the second region of interest and the first view plane;
    receiving a first user input for adjusting a position of the first indicator in the ultrasound image;
    displaying the first indicator on the adjusted position in the ultrasound image based on the first user input;
    re-determining, by the controller, a position of the second region of interest based on the adjusted position of the first indicator; and
    displaying the second indicator on the re-determined position in the ultrasound image.

2. The ultrasound medical imaging method of claim 1, wherein the predetermined number is two.

3. The ultrasound medical imaging method of claim 1, wherein the displaying the first indicator and the second indicator comprises:
    calculating a sum of pixel values in a row or a column of the ultrasound image;
    determining the positions of the plurality of regions of interest in the ultrasound image based on the sum of pixel values; and
    displaying indicators representing the plurality of regions of interest at the positions.

4. A non-transitory computer-readable recording medium that stores a program which, when executed by a computer, causes the computer to perform the ultrasound medical imaging method of claim 1.

5. The ultrasound medical imaging method of claim 1, further comprising:
    displaying a first user interface for changing a view plane of the ultrasound image;
    receiving a second user input for changing the view plane of the ultrasound image from the first view plane to a second view plane different from the first view plane through the first user interface;
    in response to the second user input, changing the view plane of the ultrasound image as the second view plane; and
    determining positions of a plurality of regions of interest corresponding to the second view plane in the ultrasound image and displaying indicators representing the plurality of regions of interest corresponding to the second view plane on the ultrasound image, based on the positions of the plurality of regions of interest corresponding to the second view plane.

6. The ultrasound medical imaging method of claim 5, wherein the first user interface comprises identification information of the plurality of view planes, and
    the identification information of the plurality of view planes is arranged on the first user interface, respectively, based on an order which is preset corresponding to the image view plane of the ultrasound image.

7. The ultrasound medical imaging method of claim 6, wherein the order is determined based on a similarity of each of the view plane images corresponding to the plurality of view planes to the one view plane image corresponding to the first view plane.

8. An ultrasound apparatus comprising:
a display;
a controller configured to:
display an ultrasound image on the display,
determine an image view plane of the ultrasound image as a first view plane, among a plurality of image view planes, by performing, in steps, a series of classifiers that classify the ultrasound image as one view plane image from a predetermined number of view plane images at each of the steps,
acquire information about a plurality of regions of interest corresponding to the first view plane,
determine positions of the plurality of regions of interest in the ultrasound image, based on the acquired information of the plurality of regions of interest, and
display a first indicator representing a first region of interest among the plurality of regions of interest and a second indicator representing a second region of interest among the plurality of regions of interest, on the ultrasound image based on the positions, wherein a form of the first indicator is determined according to the first region of interest and the first view plane and a form of the second indicator is determined according to the second region of interest and the first view plane; and
a user input unit configured to receive a first user input for adjusting a position of the first indicator in the ultrasound image,
wherein the controller is further configured to display the first indicator on the adjusted position in the ultrasound image based on the first user input, re-determine a position of the second region of interest based on the adjusted position of the first indicator, and display the second indicator on the re-determined position in the ultrasound image.

9. The ultrasound apparatus of claim 8, wherein the predetermined number is two.

10. The ultrasound apparatus of claim 8, wherein the controller is further configured to calculate a sum of pixel values in a row or a column of the ultrasound image, and determine the positions of the plurality of regions of interest in the ultrasound image based on the sum of pixel values, and display indicators representing the plurality of regions of interest at the positions.

11. The ultrasound apparatus of claim 8, wherein the controller is further configured to:
display a first user interface for changing a view plane of the ultrasound image,
receive a second user input for changing the view plane of the ultrasound image from the first view plane to a second view plane different from the first view plane through the first user interface,
in response to the second user input, change the view plane of the ultrasound image as the second view plane,
determine positions of a plurality of regions of interest corresponding to the second view plane in the ultrasound image, and
display indicators representing the plurality of regions of interest corresponding to the second view plane on the ultrasound image, based on the positions of the plurality of regions of interest corresponding to the second view plane.

12. The ultrasound apparatus of claim 11, wherein the first user interface comprises identification information of the plurality of image view planes, and
the identification information of the plurality of image view planes is arranged on the first user interface, respectively, based an order which is preset corresponding to the image view plane of the ultrasound image.

13. The ultrasound apparatus of claim 12, wherein the order is determined based on a similarity of each of the view plane images corresponding to the plurality of image view planes to the one view plane image corresponding to the first view plane.

* * * * *